(12) United States Patent
Sano et al.

(10) Patent No.: US 9,739,999 B2
(45) Date of Patent: Aug. 22, 2017

(54) VARIABLE WAVELENGTH INTERFERENCE FILTER, OPTICAL MODULE, AND OPTICAL ANALYSIS DEVICE

(71) Applicant: Seiko Epson Corporation, Tokyo (JP)

(72) Inventors: Akira Sano, Shiojiri (JP); Nozomu Hirokubo, Fujimi (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 14/954,356

(22) Filed: Nov. 30, 2015

(65) Prior Publication Data

US 2016/0085065 A1 Mar. 24, 2016

Related U.S. Application Data

(63) Continuation of application No. 14/450,815, filed on Aug. 4, 2014, now Pat. No. 9,229,220, which is a continuation of application No. 13/397,167, filed on Feb. 15, 2012, now Pat. No. 8,830,586.

(30) Foreign Application Priority Data

Feb. 16, 2011 (JP) ................................ 2011-030724

(51) Int. Cl.
*G02B 5/28* (2006.01)
*G02B 26/00* (2006.01)
*G01J 3/26* (2006.01)
*G01J 3/50* (2006.01)
(Continued)

(52) U.S. Cl.
CPC .............. *G02B 26/001* (2013.01); *G01J 3/26* (2013.01); *G01J 3/50* (2013.01); *G01J 3/51* (2013.01);
(Continued)

(58) Field of Classification Search
CPC .......... G02B 5/28; G02B 5/284; G02B 5/285; G02B 5/288
(Continued)

(56) References Cited

U.S. PATENT DOCUMENTS 7,286,244 B2 10/2007 Murata
8,830,586 B2 * 9/2014 Sano ..................... G01J 3/26
356/454

(Continued)

FOREIGN PATENT DOCUMENTS

JP 01-094312 4/1989
JP 2005-106753 A 4/2005
(Continued)

*Primary Examiner* — Jonathan Hansen
(74) *Attorney, Agent, or Firm* — Harness, Dickey & Pierce, P.L.C.

(57) ABSTRACT

An etalon is provided with a fixed substrate and a movable substrate opposed to the fixed substrate. The fixed substrate is provided with a first bonding surface to be bonded to the movable substrate via a bonding film and a first electrode surface on which a part of the first electrode is formed. The movable substrate is provided with a second bonding surface to be bonded to the first bonding surface via the bonding film and a second electrode surface on which a part of the second electrode is formed. In the state in which the fixed substrate and the movable substrate are bonded to each other with the bonding film, the first electrode formed on the first electrode surface and the second electrode formed on the second electrode surface have contact with each other.

6 Claims, 15 Drawing Sheets

(51) Int. Cl.
*G01J 3/51* (2006.01)
*H01L 27/146* (2006.01)
*G01N 21/25* (2006.01)

(52) U.S. Cl.
CPC ....... *G01N 21/25* (2013.01); *H01L 27/14621* (2013.01)

(58) Field of Classification Search
USPC ................................................ 356/454, 519
See application file for complete search history.

(56) References Cited

U.S. PATENT DOCUMENTS

| | | |
|---|---|---|
| 2007/0200146 A1 | 8/2007 | Onishi et al. |
| 2008/0253007 A1 | 10/2008 | Ohara |
| 2008/0266029 A1 | 10/2008 | Mi et al. |
| 2010/0267920 A1 | 10/2010 | Smith |
| 2010/0302660 A1 | 12/2010 | Hirokubo et al. |
| 2013/0271839 A1 | 10/2013 | Nishimura et al. |
| 2013/0279005 A1 | 10/2013 | Sano |

FOREIGN PATENT DOCUMENTS

| | | |
|---|---|---|
| JP | 2006-343686 A | 12/2006 |
| JP | 2008-076749 A | 4/2008 |
| JP | 2008-116669 A | 5/2008 |
| JP | 2008-187881 A | 8/2008 |
| JP | 2008-261951 A | 10/2008 |
| JP | 2008-278147 A | 11/2008 |
| JP | 2009-134028 A | 6/2009 |
| JP | 2011-008225 A | 1/2011 |

\* cited by examiner

VARIABLE WAVELENGTH INTERFERENCE FILTER, OPTICAL MODULE, AND OPTICAL ANALYSIS DEVICE

CROSS-REFERENCE TO RELATED APPLICATIONS

This is a continuation patent application of U.S. patent application Ser. No. 14/450,815, filed Aug. 4, 2014, which is a continuation patent application of U.S. patent application Ser. No. 13/397,167, filed Feb. 15, 2012, now U.S. Pat. No. 8,830,586, issued Sep. 9, 2014, which claims priority to Japanese Patent application No. 2011-030724, filed Feb. 16, 2011, all of which are expressly incorporated by reference herein in their entireties.

BACKGROUND

1. Technical Field

The present invention relates to a variable wavelength interference filter, an optical module equipped with the variable wavelength interference filter, and an optical analysis device equipped with the optical module.

2. Related Art

In the past, there has been known a variable wavelength interference filter having reflecting films respectively disposed on surfaces of a pair of substrates, the surfaces being opposed to each other, so as to opposed to each other via a predetermined gap, and drive electrodes respectively disposed on the surfaces of the substrates, the surfaces being opposed to each other. In such a variable wavelength interference filter, a voltage is applied between the drive electrodes to thereby control the gap between the reflecting films using the electrostatic force.

In such a variable wavelength interference filter, it is required to form an extraction electrode, which extends from each of the drive electrodes, on each of the substrates, and to provide wiring for applying the voltage to the extraction electrodes. However, since the extraction electrodes are respectively disposed on the surfaces of the pair of substrates, the surfaces being opposed to each other, there is a problem that the wiring operation becomes difficult.

Therefore, there have been proposed various configurations with which such wiring operation can easily be performed (see, e.g., JP-A-2008-261951 (Document 1)).

The device described in Document 1 is a variable shape mirror provided with a mirror substrate and a wiring substrate. The variable shape mirror is provided with the mirror substrate and the wiring substrate opposed to each other. The mirror substrate is provided with a flexible thin film having a reflecting film formed on the surface not opposed to the wiring substrate, a film-side opposed electrode disposed on the surface of the flexible thin film, the surface being opposed to the wiring substrate, and mirror substrate-side bonding pads wired to the film-side opposed electrode. Further, the wiring substrate is provided with a wiring substrate-side opposed electrode opposed to the film-side opposed electrode, wiring substrate-side bonding pads wired to the wiring substrate-side opposed electrode, and external connecting pads connected to the wiring substrate-side opposed electrode. Further, the mirror substrate-side bonding pads and the wiring substrate-side bonding pads are mechanically and electrically bonded with Au bumps, respectively.

However, in the variable shape mirror described in Document 1 mentioned above, it is required to separately dispose electrically conductive intermediate members such as Au bumps in order to electrically connecting the mirror substrate-side bonding pads and the wiring substrate-side bonding pads, and there is a problem that it is not achievable to easily and reliably make these bonding pads electrically be connected to each other.

SUMMARY

An advantage of some aspects of the invention is to provide a variable wavelength interference filter, an optical module, and an optical analysis device for making it possible to electrically connect the electrodes to each other with an easy and simple operation.

An aspect of the invention is directed to a variable wavelength interference filter including a first substrate, a second substrate opposed to the first substrate, a first reflecting film provided to a surface of the first substrate, the surface being opposed to the second substrate, a second reflecting film provided to the second substrate and opposed to the first reflecting film via a predetermined gap, a first electrode provided to a surface of the first substrate, the surface being opposed to the second substrate, and a second electrode provided to the second substrate and opposed to the first electrode, wherein the first substrate is provided with a first electrode surface on which a part of the first electrode is formed, the second substrate is provided with a second electrode surface on which a part of the second electrode is formed, and the first electrode on the first electrode surface and a second electrode on the second electrode surface have contact with each other to thereby electrically be connected to each other.

According to this aspect of the invention, the first substrate is provided with the first electrode surface on which apart of the first electrode is formed, and the second substrate is provided with the second electrode surface on which a part of the second electrode is formed. Further, since the first electrode formed on the first electrode surface and the second electrode formed on the second electrode surface have contact with each other in the state in which the substrates are bonded to each other with the bonding layer, it is not required to form an existing Au bump described above or the like for electrically connecting the electrodes to each other, and therefore, it is possible to electrically connect the electrodes to each other with a simple configuration. Further, the aspect is not limited to the configuration using a metal layer as the bonding layer, any bonding layer capable of bonding the substrates to each other can be used, and the freedom of bonding process increases.

In the variable wavelength interference filter of the above aspect of the invention, it is preferable that a region of the second substrate where the second electrode surface is formed is a flexible part having flexibility with respect to a thickness direction of the second substrate.

There is a case in which when the first electrode and the second electrode have contact with each other, a stress is applied to the second substrate due to the contact pressure. In particular, in the case in which the electrodes have pressure contact with each other in order to enhance the reliability of the electrical connection between the first electrode on the first electrode surface and the second electrode on the second electrode surface, there is a case in which a significant stress is applied to the second substrate. In contrast, in the above configuration, since the region of the second substrate where the second electrode surface is formed is the flexible section, the stress due to the contact pressure caused when the first electrode and the second electrode have contact with each other can be released by the deflection of the flexible section. Therefore, the second substrate can be prevented from deflecting due to the stress, and thus the degradation in resolution in the variable wavelength interference filter can be suppressed.

In the variable wavelength interference filter of the above aspect of the invention, it is preferable that the first substrate and the second substrate are bonded to each other via a bonding film, and a sum of a thickness dimension of the first electrode on the first electrode surface and a thickness dimension of the second electrode on the second electrode surface is larger than a thickness dimension of the bonding film.

In this configuration, since the sum of the thickness dimensions of the first electrode and the second electrode is larger than the thickness dimension of the bonding film, when the first substrate and the second substrate are bonded to each other with the bonding layer, the first electrode on the first electrode surface and the second electrode on the second electrode surface become in a state in which the first electrode and the second electrode have pressure contact with each other. Therefore, the first electrode and the second electrode can have surface contact with each other in a reliable manner by the pressure contact, and the reliability of the electrical connection can be enhanced. Further, on this occasion, since the second substrate has the flexible section, the stress applied to the second substrate by the pressure contact can be released. Further, in the case in which the flexible section has elasticity, since the reactive force (restorative force) occurs with respect to the deflection of the flexible section, it results that the first electrode and the second electrode have pressure contact with each other due to the reactive force, the reliability of electrical connection between the first electrode and the second electrode can further be enhanced.

In the variable wavelength interference filter of the above aspect of the invention, it is preferable that the first substrate has a first bonding surface disposed on a surface opposed to the second substrate, the second substrate has a second bonding surface opposed to the first bonding surface, and bonded to the first bonding surface via the bonding film, the first electrode surface and the first bonding surface are disposed coplanar with each other, and the second electrode surface and the second bonding surface are disposed coplanar with each other.

Even in the case in which there is adopted the configuration of disposing the first electrode surface and the first bonding surface at different height positions and the second electrode surface and the second bonding surface at different height positions, by controlling the thickness dimensions of the first electrode and the second electrode, the same advantage as in the above aspects of the invention can be obtained. However, in this case it is required to perform both of the formation process of the first electrode surface and the formation process of the first bonding surface in the formation process of the first substrate, and to perform both of the formation process of the second electrode surface and the formation process of the second bonding surface in the formation process of the second substrate.

In contrast, according to the above configuration, since the first electrode surface and the first bonding surface are disposed coplanar with each other, and the second electrode surface and the second bonding surface are disposed coplanar with each other, the first bonding surface and the first electrode surface or the second bonding surface and the second electrode surface can simultaneously be manufactured in the manufacturing process, thus the manufacturing process can be simplified.

In the variable wavelength interference filter of the above aspect of the invention, it is preferable that a sum of a thickness dimension of the first electrode on the first electrode surface and a thickness dimension of the second electrode on the second electrode surface is larger than a thickness dimension of the bonding film, a region of the second substrate where the second electrode surface is formed is a flexible part having flexibility with respect to a thickness direction of the second substrate, and is deflected in a direction away from the first electrode surface.

According to this configuration, when the substrate are bonded to each other via the bonding film, the flexible part is deflected in the direction away from the first electrode surface, and the first electrode surface and the second electrode surface become in the state in which the first electrode surface and the second electrode surface have pressure contact with each other. Therefore, the first electrode and the second electrode formed on the respective electrode surfaces can electrically be connected to each other in a reliable manner.

Another aspect of the invention is directed to an optical module including the variable wavelength interference filter according to any of the configurations described above, and a light receiving section adapted to receive a test target light transmitted through the variable wavelength interference filter.

According to this aspect of the invention, as described above, since in the variable wavelength interference filter, the electrical connection between the electrodes can be achieved with a simple structure, contribution to the simplification of the structure of the optical module can also be made. Thus, in the optical module, if, for example, the first electrode and the second electrode are drive electrodes for controlling the gap, since the gap can be kept with accuracy, in the optical module equipped with such a variable wavelength interference filter, light intensity measurement with high accuracy can be performed by the light receiving section.

In the optical module of the above aspect of the invention, it is preferable that there is further provided a pressing section adapted to press the first electrode surface and the second electrode surface in a direction of coming closer to each other.

According to this configuration, since the pressing section presses the electrode surfaces in the direction in which the electrode surfaces come closer to each other, the electrode surfaces are in the state of having pressure contact with each other, and the electrical connection between the first electrode and the second electrode formed on the respective electrode surfaces becomes reliable.

In the optical module of the above aspect of the invention, it is preferable that there is further provided a housing chassis adapted to house the variable wavelength interference filter, and the pressing section is provided to the housing chassis.

In general, when assembling the variable wavelength interference filter into the optical module, the housing chassis housing the variable wavelength interference filter is often incorporated in the optical module.

According to the above configuration, since the pressing section is provided to the housing chassis, there is no need for separately providing the pressing section to the main body of the optical module, and therefore, the configuration can be simplified.

Still another aspect of the invention is directed to an optical analysis device including an optical module of the above aspect of the invention, and an analysis processing section adapted to analyze optical characteristics of the test target light based on the light received by the light receiving section of the optical module.

According to this aspect of the invention, since the optical module having the variable wavelength interference filter described above is provided, measurement with high accuracy can be preformed, and by performing the optical analysis processing based on the measurement result, accurate spectral characteristics can be obtained.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

A first embodiment of the invention will hereinafter be explained with reference to the accompanying drawings.

1. Schematic Configuration of Colorimetric Device

Figure 1:
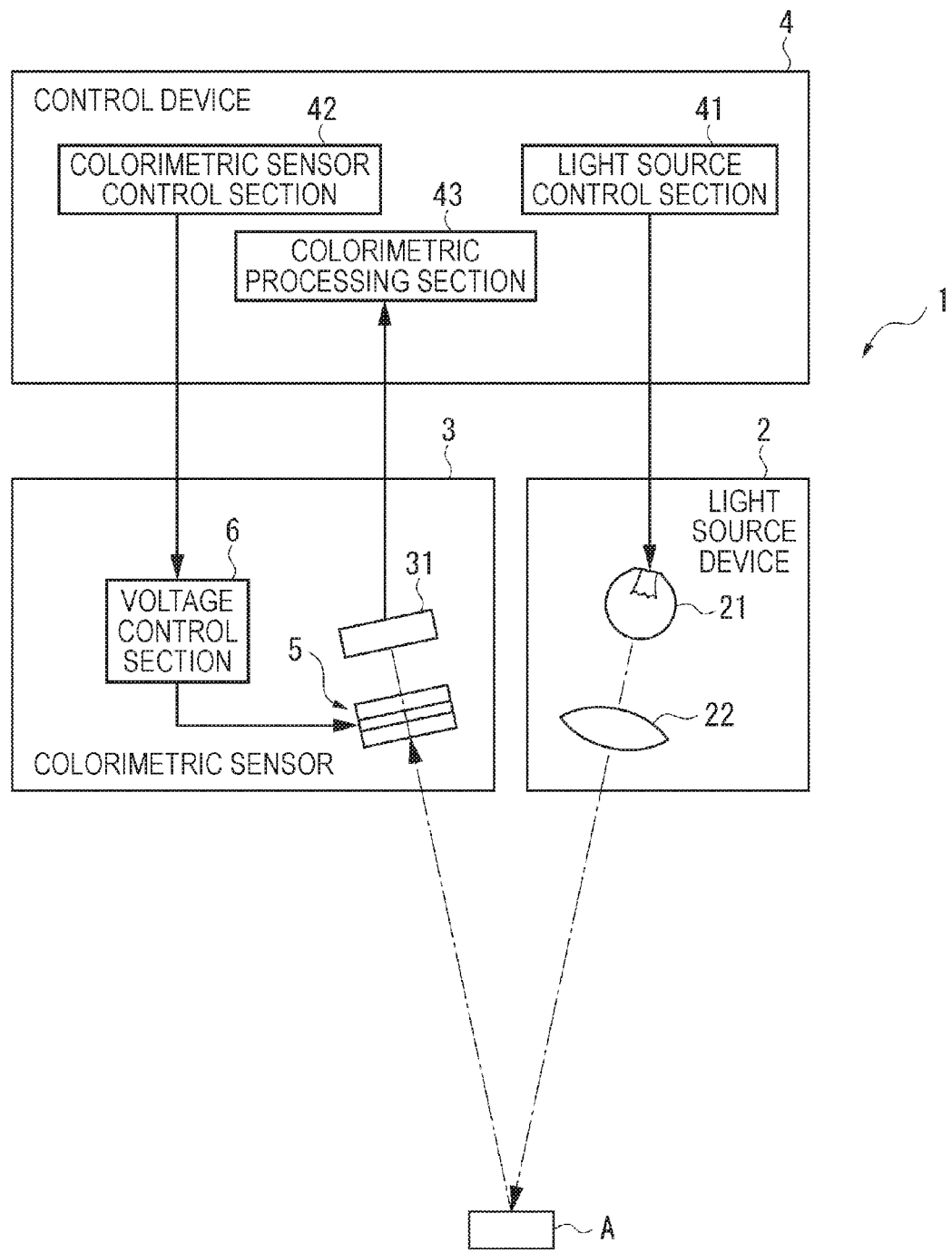
FIG. 1 is a block diagram showing a schematic configuration of a colorimetric device according to a first embodiment of the invention.

FIG. 1 is a block diagram showing a schematic configuration of a colorimetric device 1 (an optical analysis device) according to the present embodiment.

As shown in FIG. 1, the colorimetric device 1 is provided with a light source device 2 for emitting light to a test object A, a colorimetric sensor 3 (an optical module), and a control device 4 for controlling an overall operation of the colorimetric device 1. Further, the colorimetric device 1 is a device for making the light, which is emitted from the light source device 2, be reflected by the test object A, receiving the test target light thus reflected using the colorimetric sensor 3, and analyzing and then measuring the chromaticity of the test target light, namely the color of the test object A, based on the detection signal output from the colorimetric sensor 3.

2. Configuration of Light Source Device

The light source device 2 is provided with a light source 21 and a plurality of lenses 22 (one of the lenses is shown alone in FIG. 1), and emits a white light to the test object A. Further, it is possible for the plurality of lenses 22 to include a collimator lens, and in this case, the light source device 2 converts the white light emitted from the light source 21 into a parallel light with the collimator lens, and emits it from the projection lens not shown toward the test object A. It should be noted that although in the present embodiment the colorimetric device 1 provided with the light source device 2 is described as an example, in the case, for example, in which the test object A is a light emitting member such as a liquid crystal panel, it is also possible to adopt the configuration not provided with the light source device 2.

3. Configuration of Colorimetric Sensor

As shown in FIG. 1, the colorimetric sensor 3 is provided with an etalon 5 (a variable wavelength interference filter), a light receiving element 31 (a light receiving section) for receiving the light transmitted through the etalon 5, and a voltage control section 6 for varying the wavelength of the light to be transmitted through the etalon 5. Further, the colorimetric sensor 3 is provided with an entrance optical lens not shown disposed at a position opposed to the etalon 5, the entrance optical lens guiding the reflected light (the test target light) reflected by the test object A into the inside thereof. Further, the colorimetric sensor 3 disperses the light with a predetermined wavelength out of the test target light entering from the entrance optical lens using the etalon 5, and then receives the light thus dispersed using the light receiving element 31.

The light receiving element 31 is composed of a plurality of photoelectric conversion elements, and generates an electric signal corresponding to the received light intensity. Further, the light receiving element 31 is connected to the control device 4, and outputs the electric signal thus generated to the control device 4 as a light reception signal.

3-1. Configuration of Etalon

Figure 2:
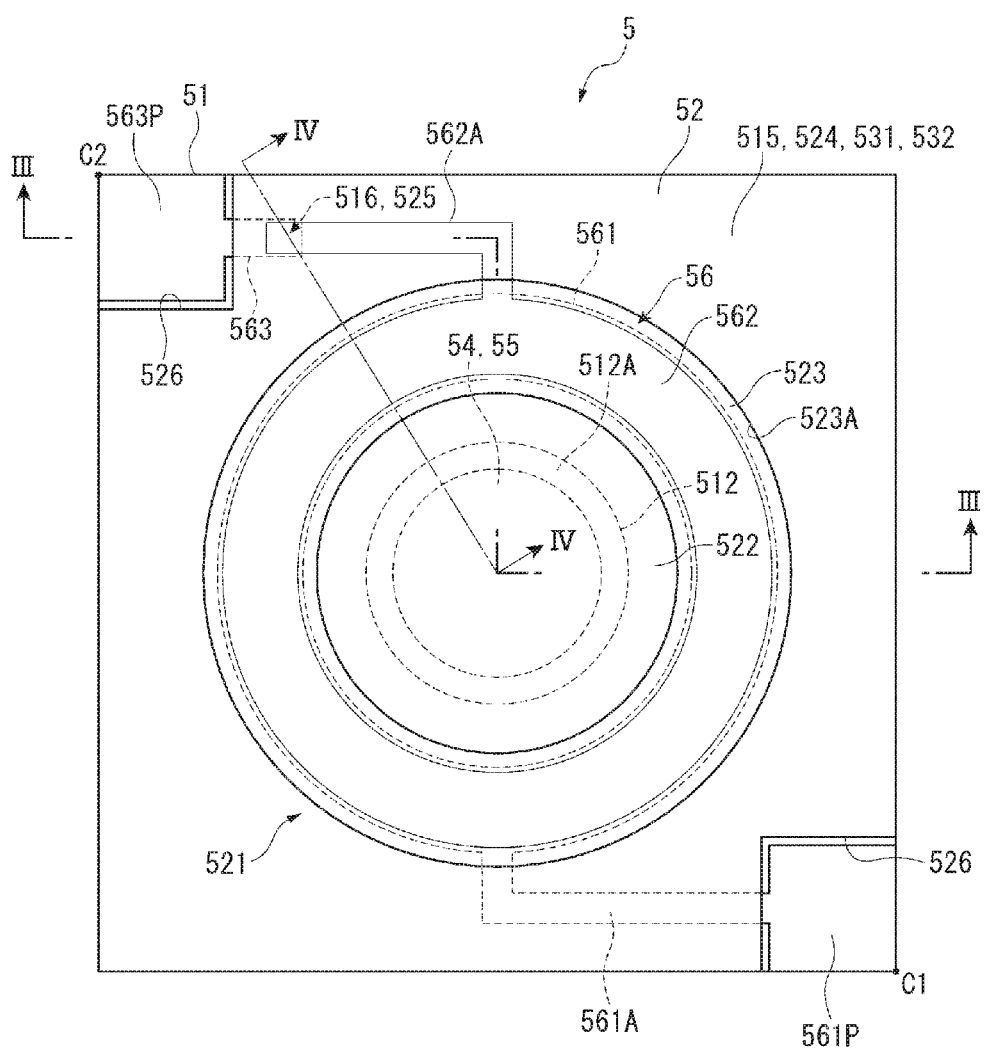
FIG. 2 is a plan view of an etalon according to the first embodiment.
Figure 3:
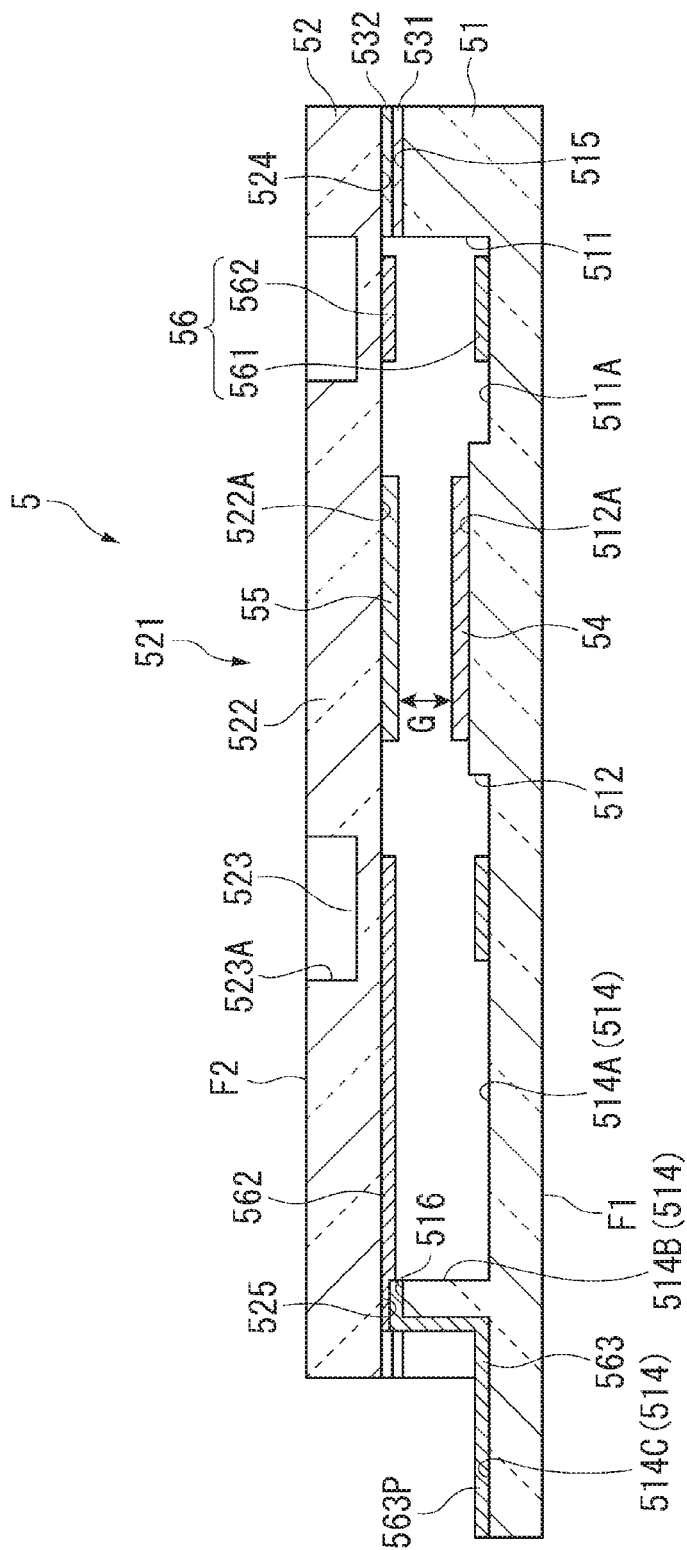
FIG. 3 is a schematic cross-sectional view of the etalon according to the first embodiment.

FIG. 2 is a plan view of the etalon 5, and FIG. 3 is a schematic cross-sectional view of the etalon 5 at a position indicated by the arrowed line III-III shown in FIG. 2. Further, FIG. 4 is a partial cross-sectional view of the etalon 5 at a position indicated by the arrowed line IV-IV shown in FIG. 2.

As shown in FIG. 2, the etalon 5 is a plate-like optical member having a square planar shape formed to be, for example, 10 mm on a side. As shown in FIG. 3, the etalon 5 is provided with a fixed substrate 51 (a first substrate) and a movable substrate 52 (a second substrate). These two substrates 51, 52 are constituted integrally with a first bonding surface 515 and a second bonding surface 524 bonded to each other via a first bonding film 531 and a second bonding film 532 by siloxane bond using a plasma-polymerized film. These two substrates 51, 52 are each made of glass of various types such as soda glass, crystalline glass, quartz glass, lead glass, potassium glass, borosilicate glass, or alkali-free glass, or a quartz crystal, for example. It should be noted that the bonding film of the embodiment of the invention is composed of the first bonding film 531 and the second bonding film 532.

Figure 4:
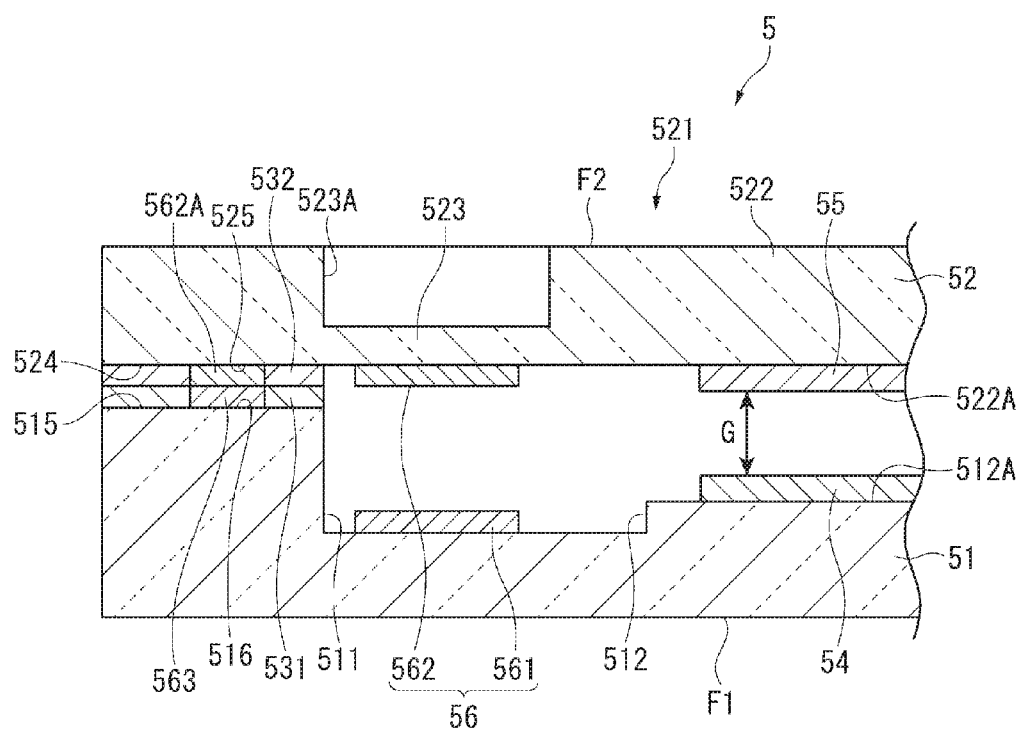
FIG. 4 is a partial cross-sectional view of the etalon according to the first embodiment.

Further, as shown in FIG. 4, between the fixed substrate 51 and the movable substrate 52, there are disposed a fixed mirror 54 (a first reflecting film) and a movable mirror 55 (a second reflecting film). Here, the fixed mirror 54 is fixed to a surface of the fixed substrate 51 opposed to the movable substrate 52, and the movable mirror 55 is fixed to a surface of the movable substrate 52 opposed to the fixed substrate 51. Further, the fixed mirror 54 and the movable mirror 55 are disposed so as to be opposed to each other via an inter-mirror gap G.

Further, an electrostatic actuator 56 for controlling the dimension of the inter-mirror gap G between the fixed mirror 54 and the movable mirror 55 is disposed between the fixed substrate 51 and the movable substrate 52.

3-1-1. Configuration of Fixed Substrate

Figure 5:
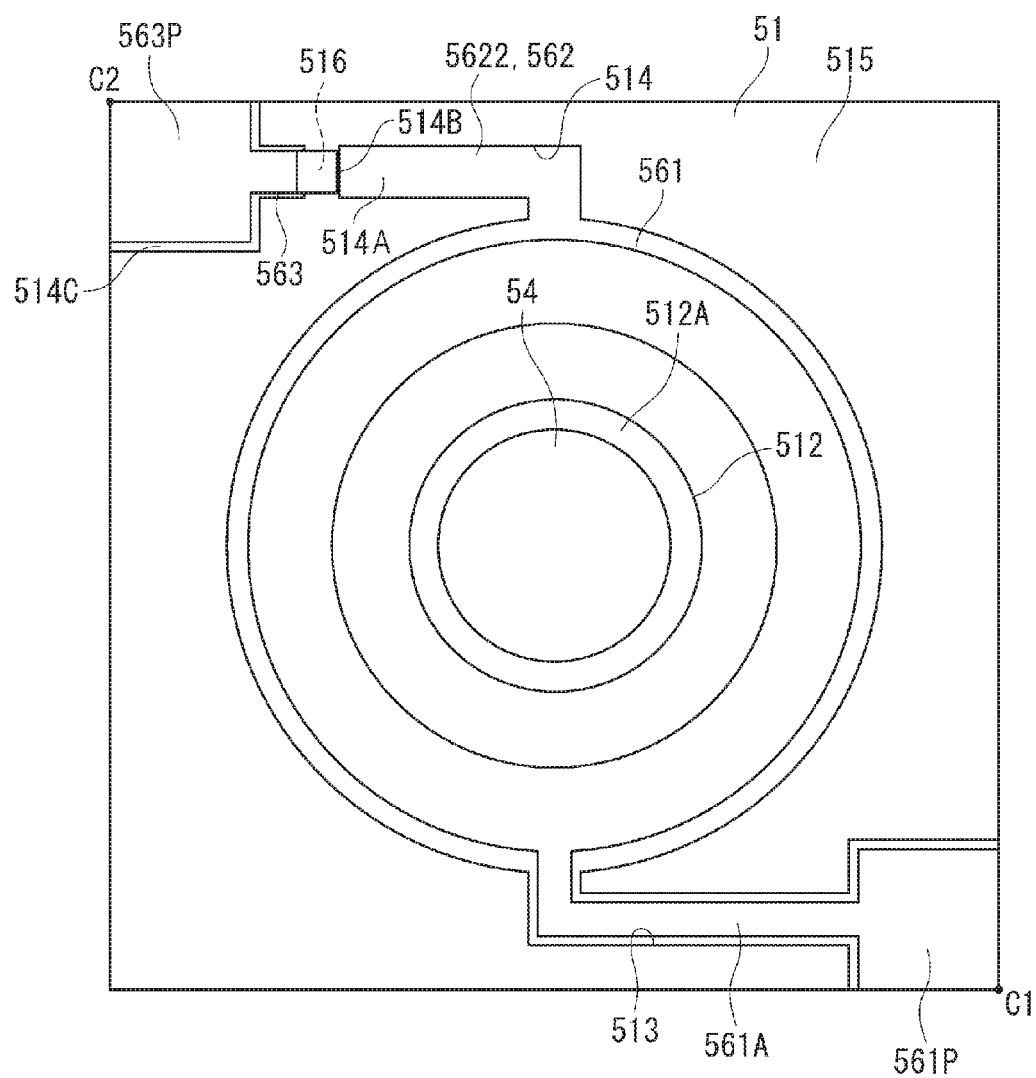
FIG. 5 is a plan view of a fixed substrate of the etalon according to the first embodiment viewed from a movable substrate side.

FIG. 5 is a plan view of the fixed substrate 51 viewed from the movable substrate 52 side.

The fixed substrate 51 is formed by processing a quartz glass substrate with a thickness of, for example, 500 μm using an etching process. As shown in FIGS. 3 through 5, the fixed substrate 51 is provided with an electrode formation groove 511 and a mirror fixation section 512 using the etching process.

Further, the fixed substrate 51 is provided with a first extraction formation section 513 extending from the peripheral edge of the electrode formation groove 511 toward one vertex (the vertex C1 in FIG. 5) of the fixed substrate 51, and a second extraction formation section 514 extending toward a vertex C2 having a diagonal relationship with the vertex C1.

Further, in the fixed substrate 51, the portion where neither of the electrode formation groove 511, the mirror fixation section 512, the first extraction formation section 513, nor the second extraction formation section 514 is formed corresponds to the first bonding surface 515 of the fixed substrate 51.

The first extraction formation section 513 is a groove formed to have the same depth dimension as that of the electrode formation groove 511 by an etching process. The first extraction formation section 513 is provided with a first extraction electrode 561A described later.

The second extraction formation section 514 is provided with an extending groove 514A extending from the peripheral edge of the electrode formation groove 511, a projection section 514B contiguous to the extending tip of the extending groove 514A, and a pad section 514C contiguous to the projection section 514B.

The extending groove 514A is a groove formed to have the same depth dimension as that of the electrode formation groove 511 by an etching process, and is formed to have an L shape.

The projection section 514B is an area on which the etching process is not performed, and is a region projecting toward the movable substrate 52 closer thereto than the extending groove 514A and the pad section 514C. The surface of the projection section 514B opposed to the movable substrate 52 becomes coplanar with the first bonding surface 515 to form a first electrode surface 516.

The pad section 514C is a groove formed to have the same depth dimension as that of the electrode formation groove 511 by the etching process. It should be noted that although in the present embodiment the shape of the pad section 514C etched to be coplanar with the electrode formation groove 511 is described as an example, this is not a limitation, and the configuration in which the pad section 514C is formed to be coplanar with the first electrode surface 516 can also be adopted.

The second extraction formation section 514 described above has the configuration in which the first bonding surface 515 is formed between the first electrode surface 516 of the projection section 514B and the electrode formation groove 511 as shown in FIG. 2.

As shown in FIG. 3, the electrode formation groove 511 is provided with an electrode fixation surface 511A having a ring-like shape formed between the peripheral edge of the mirror fixation section 512 to the inner circumferential wall surface of the electrode formation groove 511. As shown in FIGS. 2 through 4, the electrode fixation surface 511A is provided with a first drive electrode 561 having a ring-like shape formed on the electrode fixation surface 511A.

The first drive electrode 561 is an electrically conductive film, and indium tin oxide (ITO), a metal laminated body made of Au/Cr or the like, a laminated body of ITO and Au/Cr, and so on can be used therefor. Further, it is also possible to adopt the configuration in which an insulating film (not shown) for preventing leakage due to the discharge between the first and second drive electrodes 561, 562 and so on is formed on the upper surface of the first drive electrode 561. As such an insulating film, $SiO_2$, tetraethoxysilane (TEOS), and so on can be used.

As shown in FIGS. 2 and 5, the first extraction electrode 561A extending toward the vertex C1 of the fixed substrate 51 is formed along the first extraction formation section 513 from a part of the peripheral edge of the first drive electrode 561. Further, at the tip of the first extraction electrode 561A, there is formed a first electrode pad 561P, and the first electrode pad 561P is connected to the voltage control section 6 (see FIG. 1). Further, when driving the electrostatic actuator 56, the voltage control section 6 (see FIG. 1) applies a voltage to the first electrode pad 561P to thereby apply a voltage to the first drive electrode 561.

Further, the second extraction formation section 514 of the fixed substrate 51 is provided with a first conductive electrode 563 constituting a first electrode according to the invention.

Specifically, the first conductive electrode 563 is an electrode isolated from the first drive electrode 561, and is formed throughout the area from the pad section 514C of the first extraction formation section 514 to the first electrode surface 516 of the projection section 514B. Further, the first conductive electrode 563 disposed on the first electrode surface 516 has surface contact with a second extraction electrode 562A described later disposed on a second electrode surface 525 described later of the movable substrate 52. Thus, the state in which the first conductive electrode 563 and the second drive electrode 562 are electrically connected to each other is made. Therefore, by adopting a material with lower electrical resistance as the material of the surfaces of the first conductive electrode 563 and the second extraction electrode 562A, the contact resistance of the portion having surface contact described above can be reduced to thereby eliminate intervention of an unwanted resistance component, and thus reliable electrical conduction can be obtained. As such a material, there can be selected a metal film made of Au or the like, a metal laminated body made of Au/Cr or the like, or a material having a configuration of stacking a metal material such as Au or a metal laminated body made of Au/Cr on a surface of a metal oxide such as ITO. It should be noted that it is also possible to adopt a configuration of stacking a metal film or a metal laminated film on the electrode made of a metal oxide such as ITO locally around the area having surface contact described above.

Further, the area on the pad section 514C of the first conductive electrode 563 constitutes a conductive electrode pad 563P, and is connected to piezoelectric control section 6 (see FIG. 1). Further, when driving the electrostatic actuator 56, the voltage control section 6 applies a voltage to the conductive electrode pad 563P to thereby apply the voltage to the second drive electrode 562.

As shown in FIGS. 2 and 3, the mirror fixation section 512 is formed to have a roughly columnar shape having a redial dimension smaller than that of the electrode formation groove 511 and coaxial with the electrode formation groove 511, and is provided with a mirror fixation surface 512A disposed on a surface thereof opposed to the movable substrate 52. It should be noted that although in the present embodiment there is shown an example in which the mirror fixation surface 512A of the mirror fixation section 512 opposed to the movable substrate 52 is formed nearer to the movable substrate 52 than the electrode fixation surface 511A as shown in FIG. 3, the structure is not limited thereto. The height positions of the electrode fixation surface 511A and the mirror fixation surface 512A are arbitrarily set in accordance with the dimension of the gap between the fixed mirror 54 fixed to the mirror fixation surface 512A and the movable mirror 55 formed on the movable substrate 52, the dimension of a distance between the first drive electrode 561 and the second drive electrode 562, the thickness dimensions of the fixed mirror 54 and the movable mirror 55, and so on. Therefore, there can be adopted, for example, a configuration in which the electrode fixation surface 511A and the mirror fixation surface 512A are formed coplanar with each other, or a configuration in which the mirror fixation groove shaped like a cylindrical recessed groove is formed in the central portion of the electrode fixation surface 511A, and the mirror fixation surface is formed on the bottom surface of the mirror fixation groove.

Further, to the mirror fixation surface 512A, there is fixed the fixed mirror 54 formed of a single layer of an AgC alloy having a circular shape capable of covering the entire visible range as the wavelength range of the light which can be dispersed. It should be noted that although in the present embodiment there is described an example in which the mirror made of the AgC alloy single layer is used as the fixed mirror 54, it is also possible to adopt a configuration of using a mirror formed of a $TiO_2$—$SiO_2$ type dielectric multilayer film, an Ag alloy other than the AgC alloy, or a laminated film composed of an Ag alloy film and a dielectric film.

As shown in FIGS. 3 and 4, the first bonding surface 515 and the first electrode surface 516 are formed to have the same height dimension from a first reference surface F1, which is a surface of the fixed substrate 51, and is not opposed to the movable substrate 52. In other words, the first bonding surface 515 and the first electrode surface 516 are formed to be coplanar with each other.

A first bonding film 531 of a plasma-polymerized film having polyorganosiloxane used as a chief material is formed on the first bonding surface 515 as a main material.

3-1-2. Configuration of Movable Substrate

Figure 6:
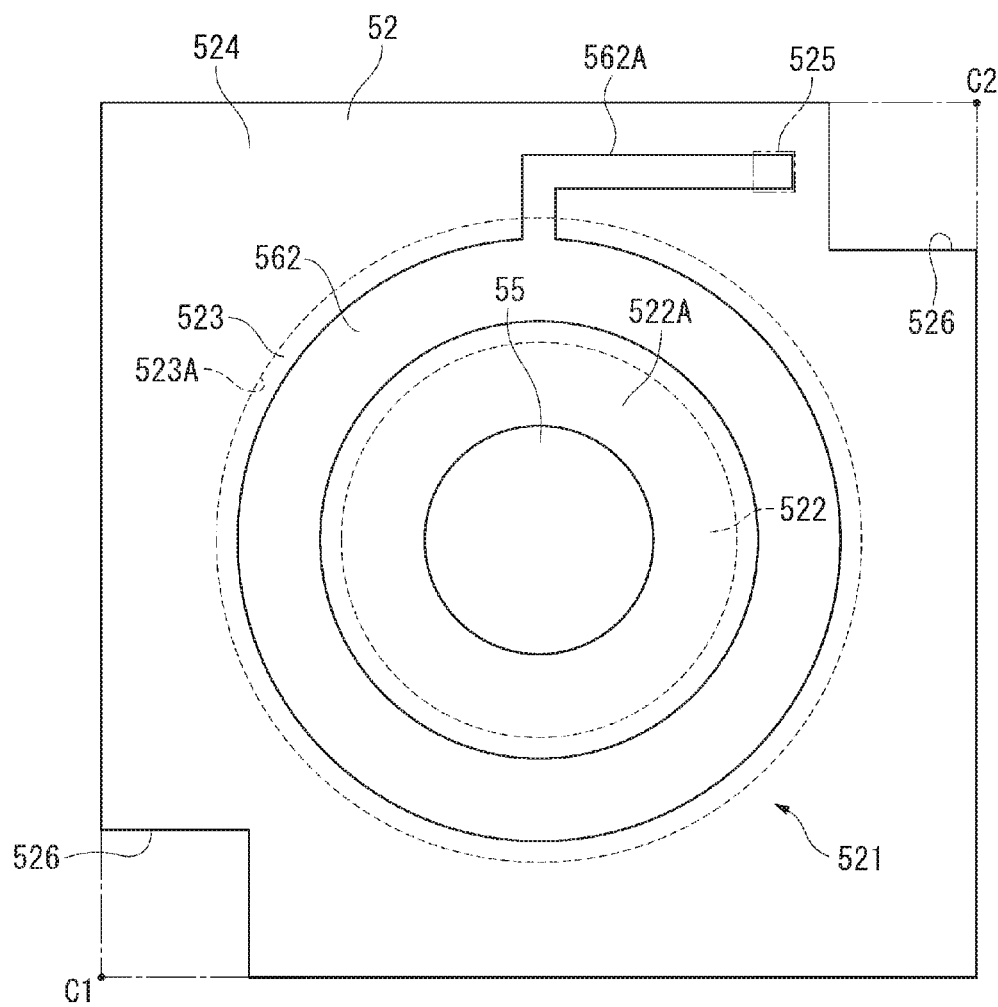
FIG. 6 is a plan view of the movable substrate of the etalon according to the first embodiment viewed from the fixed substrate side.

FIG. 6 is a plan view of the movable substrate 52 viewed from the fixed substrate 51 side.

The movable substrate 52 is formed by processing a glass substrate with a thickness of, for example, 200 μm using an etching process. The movable substrate 52 is provided with a displacement section 521 having a circular shape centered on the substrate center point in a plan view, for example. As shown in FIGS. 2, 3, and 6, the displacement section 521 is provided with a connection holding section 523, which is coaxial with the movable section 522 having a columnar shape and moving back and forth toward the fixed substrate 51, and is formed to have an annular shape in the etalon plan view so as to hold the movable section 522 movably in the thickness direction of the movable substrate 52.

Further, in the surface of the movable substrate 52 opposed to the fixed substrate 51, an area opposed to the first bonding surface 515 of the fixed substrate 51 forms the second bonding surface 524 in the movable substrate 52, and an area opposed to the first electrode surface 516 of the fixed substrate forms the second electrode surface 525 in the movable substrate 52.

Further, the movable substrate 52 is provided with cut sections 526 at the positions of the vertexes C1, C2, and the first electrode pad 561P and the first conductive electrode pad 563P are exposed in a plan view of the etalon 5 viewed from the movable substrate 52 side.

The displacement section 521 is formed by providing a groove to glass substrate having a plate-like shape, which is a constituent material of the second substrate 52, using an etching process. In other words, the displacement section 521 is formed by providing the surface of the movable substrate 52, the surface being not opposed to the fixed substrate 51, with an annular groove section 523A having an annular shape for forming the connection holding section 523 using an etching process.

The movable section 522 is formed to have a thickness dimension larger than that of the connection holding section 523, and is formed in the present embodiment, for example, to have the thickness dimension of 200 μm, the same dimension as the thickness dimension of the movable substrate 52. The movable section 522 is formed to have a radial dimension larger than the radial dimension of the mirror fixation section 512 of the fixed substrate 51.

The surface of the movable section 522 opposed to the fixed substrate 51 is provided with a movable surface 522A parallel to the mirror fixation surface 512A of the fixed substrate 51, and the movable surface 522A is provided with the movable mirror 55 having the same configuration as that of the fixed mirror 54.

The connection holding section 523 is a diaphragm surrounding the periphery of the movable section 522, and is formed to have a thickness dimension of, for example, 50 μm. The second drive electrode 562 is formed on a surface of the connection holding section 523 opposed to the fixed substrate 51 and the second electrode surface 525. It should be noted that although the connection holding section 523 shaped like a diaphragm is shown as an example in the present embodiment, it is also possible to adopt, for example, a configuration provided with a connections holding section having a plurality of pairs of beam structures disposed at positions point-symmetrical about the center of the movable section 522.

As shown in FIGS. 2 through 4, the second drive electrode 562 is a ring-like electrode formed on a surface of the connection holding section 523 opposed to the fixed substrate 51.

The second drive electrode 562 is formed to have the same configuration as those of the first drive electrode 561 and the first conductive electrode 563, and constitutes the electrostatic actuator 56 together with the first drive electrode 561. As shown in FIGS. 2 and 6, the second extraction electrode 562A (constituting the second electrode according to the invention) bent to form an L shape is formed extending from a part of the peripheral edge of the second drive electrode 562. As shown in FIGS. 2 and 6, the second extraction electrode 562A extends to the second electrode surface 525 as the area opposed to the first electrode surface 516 on the surface of the movable substrate 52 opposed to the fixed substrate 51.

As shown in FIGS. 3 and 4, the second bonding surface 524 and the second electrode surface 525 are formed to have the same height dimension from a second reference surface F2, which is a surface of the movable substrate 52, and is not opposed to the fixed substrate 51. In other words, the second bonding surface 524 and the second electrode surface 525 are formed to be coplanar with each other.

Similarly to the first bonding surface 515 of the fixed substrate 51, the second bonding surface 524 is provided with the second bonding film 532 having polyorganosiloxane used as a chief material, and the substrates 51, 52 are bonded to each other by bonding the bonding surfaces 515, 524 to each other via the first bonding film 531 and the second bonding film 532. It should be noted that it is also possible to adopt a configuration in which the second bonding film 532 is not formed in the area opposed to the first extraction electrode 561A or the first conductive electrode 563.

Further, the second extraction electrode 562A has surface contact with the first conductive electrode 563 formed on the first electrode surface 516 to thereby be electrically connected thereto in the condition in which the first bonding surface 515 of the fixed substrate 51 and the second bonding surface 524 of the movable substrate 52 are bonded to each other with the bonding films 531, 532.

On this occasion, the first conductive electrode 563 of the first electrode surface 516 and the second extraction electrode 562A of the second electrode surface 525 are in a condition of having pressure contact in a direction of coming closer to each other. Thus, it results that the first conductive electrode 563 and the second extraction electrode 562A are electrically connected to each other in a reliable manner.

Further, as shown in FIG. 4, in the etalon 5 according to the present embodiment, the first bonding surface 515 is disposed in a straight area between the first electrode surface 516 and the electrode formation groove 511 of the fixed substrate 51, and is bonded to the second bonding surface 524 of the movable substrate 52. Therefore, as described above, even in the case in which the electrodes have pressure contact with each other and the reactive force thereof is applied to the movable substrate 52, the reactive force is not propagated to the connection holding section 523, and thus the deflection of the connection holding section 523 and the tilt of the movable section 522 can be prevented.

3-1-3. Connection Between Etalon and Voltage Control Section

In the connection between the etalon 5 described above and the voltage control section 6, lead wires connected to the voltage control section 6 are connected respectively to the two pads, namely the first electrode pad 561P and the first conductive electrode pad 563P, by, for example, wire bonding.

Here, the movable substrate 52 of the etalon 5 is provided with the cut sections 526 formed by cutting the areas opposed to the first electrode pad 561P and the first conductive electrode pad 563P, respectively. Therefore, when connecting the lead wires to the etalon 5, it becomes possible to eliminate a cumbersome operation such as insertion of the lead wires between the fixed substrate 51 and the movable substrate 52, and it becomes possible to directly establish the connection to the first electrode pad 561P and the first conductive electrode pad 563P directly from the light entrance side surface of the etalon 5. Further, in the wiring work, the spaces provided by cutting the movable substrate 52 as the cut sections 526 are used as the working spaces. Therefore, the wiring work to the etalon 5 can easily be performed.

3-2. Configuration of Voltage Control Section

The voltage control section 6 controls the voltage to be applied to the first drive electrode 561 and the second drive electrode 562 of the electrostatic actuator 56 based on a control signal input from the control device 4.

4. Configuration of Control Device

The control device 4 controls an overall operation of the colorimetric device 1. As the control device 4, a general-purpose personal computer, a handheld terminal, a colorimetry-dedicated computer, and so on can be used.

Further, as shown in FIG. 1, the control device 4 is configured including a light source control section 41, a colorimetric sensor control section 42, a colorimetric processing section 43 (an analysis processing section), and so on.

The light source control section 41 is connected to the light source device 2. Further, the light source control section 41 outputs a predetermined control signal to the light source device 2 based on, for example, a setting input by the user to thereby make the light source device 2 emit a white light with a predetermined brightness.

The colorimetric sensor control section 42 is connected to the colorimetric sensor 3. Further, the colorimetric sensor control section 42 sets the wavelength of the light to be received by the colorimetric sensor 3 based on, for example, the setting input by the user, and then outputs the control signal instructing the detection of the intensity of the received light having the wavelength thus set to the colorimetric sensor 3. Thus, the voltage control section 6 of the colorimetric sensor 3 sets the voltage to be applied to the electrostatic actuator 56 based on the control signal so as to transmit the light having the wavelength desired by the user.

The colorimetric processing section 43 controls the colorimetric sensor control section 42 to vary the inter-mirror gap of the etalon 5 to thereby vary the wavelength of the light transmitted through the etalon 5. Further, the colorimetric processing section 43 obtains the light intensity of the light transmitted through the etalon 5 based on a light reception signal input from the light receiving element 31. Then, the colorimetric processing section 43 calculates the chromaticity of the light reflected by the test object A based on the intensity of the received light having each of the wavelengths obtained as described above.

5. Method of Manufacturing Etalon

Then, the method of manufacturing the etalon 5 described above will be explained with reference to FIGS. 7A through 7E, and 8A through 8F.

In order to manufacture the etalon 5, the fixed substrate 51 and the movable substrate 52 are separately manufactured, and then the fixed substrate 51 and the movable substrate 52 thus manufactured are bonded to each other.

5-1. Fixed Substrate Manufacturing Process

Figure 7A:
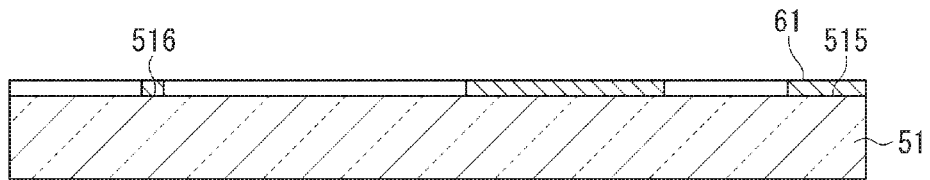
FIGS. 7A through 7E are diagrams showing a manufacturing process of the fixed substrate of the etalon according to the first embodiment.

Firstly, a quartz glass substrate with a thickness dimension of 500 μm as a manufacturing material of the fixed substrate 51 is prepared, and fine polishing is performed on both surfaces thereof until the surface roughness Ra of the quartz glass substrate becomes 1 nm or lower. Further, a resist 61 for forming the electrode formation groove 511 is applied to the surface of the fixed substrate 51 opposed to the movable substrate 52, then the resist 61 thus applied is exposed and then developed using a photolithography process to thereby pattern the places where the electrode formation groove 511, the first extraction formation section 513, the extending groove 514A, and the pad section 514C are formed as shown in FIG. 7A.

Figure 7B:
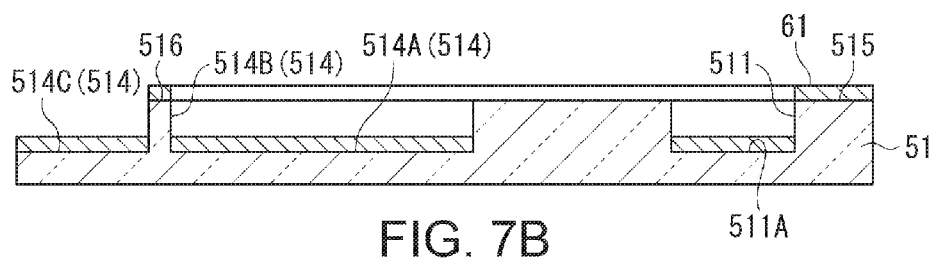

Then, as shown in FIG. 7B, the electrode formation groove 511, the first extraction formation section 513, the extending groove 514A, and the pad section 514C are etched to have a desired depth. It should be noted that as the etching process here, a wet-etching process using an etching liquid such as HF is used.

Further, a resist 61 for forming the mirror fixation surface 512A is applied to the surface of the fixed substrate 51 opposed to the movable substrate 52, then the resist 61 thus applied is exposed and then developed using a photolithography process to thereby be patterned to form the mirror fixation surface 512A as shown in FIG. 7B.

Figure 7C:
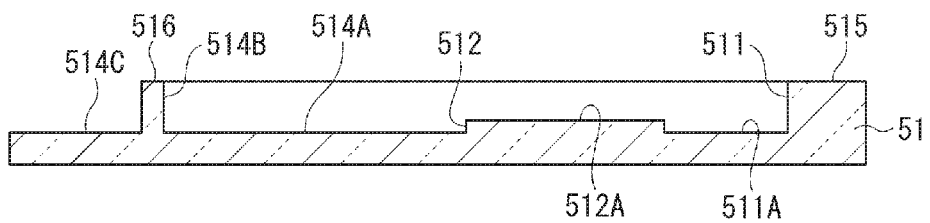

Then, after etching the mirror fixation surface 512A to a desired position, the resist 61 is removed as shown in FIG. 7C to thereby form the electrode fixation surface 511A, the mirror fixation surface 512A, the first bonding surface 515, and the first electrode surface 516, and thus determine the substrate shape of the fixed substrate 51.

Figure 7D:
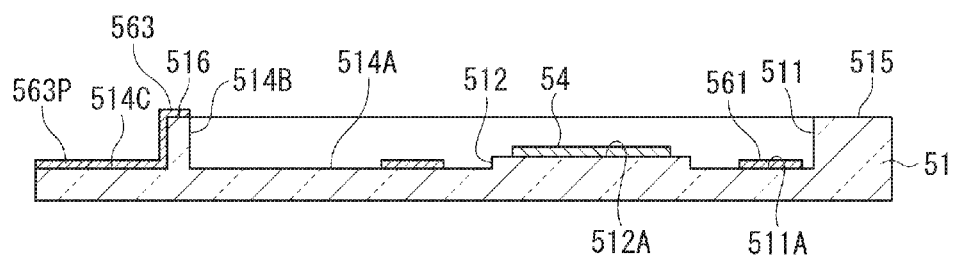

Subsequently, as shown in FIG. 7D, the first drive electrode 561 is formed on the electrode fixation surface 511A, and the first conductive electrode 563 is formed throughout the area from the pad section 514C to the first electrode surface 516. Further, the fixed mirror 54 is formed on the mirror fixation surface 512A.

For example, in the formation of the first electrode 561 and the first conductive electrode 563, an Au/Cr laminated film is deposited on the fixed substrate 51 using a sputtering process, then a resist having a desired electrode pattern is formed on the Au/Cr laminated film, and then a photo-etching process is performed on the Au/Cr laminated film.

Further, the fixed mirror 54 is formed by a lift-off process. Specifically, a resist (a lift-off pattern) is formed on the fixed substrate 51 in an area other than the mirror formation section using a photolithography process or the like, and then a $TiO_2$—$SiO_2$ type of thin film is deposited using a sputtering process or an evaporation process. Then, after forming the fixed mirror 54, the thin film in the other area than the mirror fixation surface 512A is removed by lift-off.

Figure 7E:
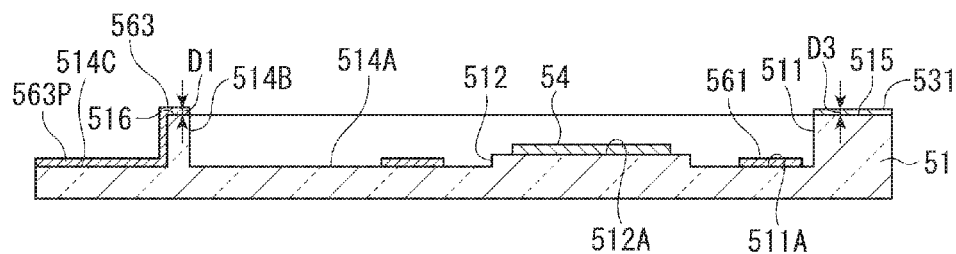

Subsequently, a resist 61 (a lift-off pattern) is formed on the fixed substrate 51 in an area other than the formation section of the first bonding film 531 using a photolithography process or the like, and then a plasma-polymerized film using polyorganosiloxane with a thickness dimension D3 is deposited using a plasma CVD process or the like. Then, by removing the resist 61, the first bonding film 531 is formed on the first bonding surface 515 as shown in FIG. 7E.

According to the process described above, the fixed substrate 51 is formed.

5-2. Movable Substrate Manufacturing Process

Figure 8A:
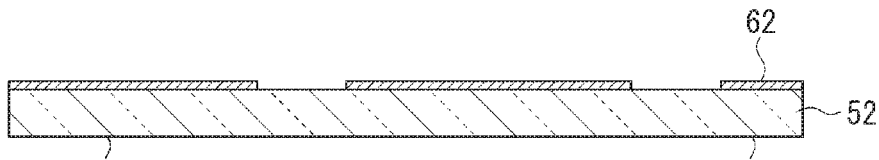
FIGS. 8A through 8F are diagrams showing a manufacturing process of the movable substrate of the etalon according to the first embodiment.

Firstly, a quartz glass substrate with a thickness dimension of 200 μm as a manufacturing material of the movable substrate 52 is prepared, and fine polishing is performed on both surfaces thereof until the surface roughness Ra of the quartz glass substrate becomes 1 nm or lower. Then, a resist 62 is applied to the entire surface of the movable substrate 52, and the resist 62 thus applied is exposed and then developed to thereby be patterned to form the connection holding section 523 as shown in FIG. 8A.

Figure 8B:
Figure 8C:

Subsequently, by performing a wet-etching process on the quartz glass substrate, the connection holding section 523 with a thickness of 50 μm is formed, and at the same time, the movable section 522 is formed as shown in FIG. 8B. Then, as shown in FIG. 8C, by removing the resist 62, the substrate shape of the movable substrate 52 provided with the movable section 522 and the connection holding section 523 is determined.

Figure 8D:
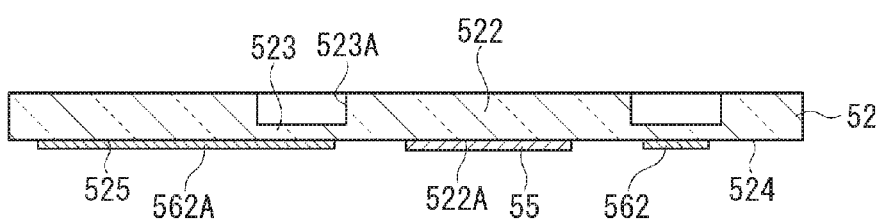

Subsequently, as shown in FIG. 8D, the second drive electrode 562 is formed in the connection holding section 523 on the surface opposed to the fixed substrate 51, and the second extraction electrode 562A extending from apart of the peripheral edge of the second drive electrode 562 toward the second electrode surface 525 is formed. Further, the movable mirror 55 is formed on the movable surface 522A.

Specifically, an Au/Cr laminated film is formed on the surface of the movable substrate 52 opposed to the fixed substrate 51 using a sputtering process or the like. Then, by forming a resist to form a desired electrode pattern is formed on the Au/Cr laminated film, and then performing a photo-etching process on the Au/Cr laminated film, the second electrode 562 with a thickness dimension D2 is formed on the surface opposed to the fixed substrate 51 in the connection holding section 523 as shown in FIG. 8D. Subsequently, the resist remaining on the surface of the movable substrate 52 opposed to the fixed substrate 51 is removed.

Further, the movable mirror 55 is formed by a lift-off process or the like. Specifically, a resist (a lift-off pattern) is formed on the movable substrate 52 in an area other than the mirror formation section using a photolithography process or the like, and then a $TiO_2$—$SiO_2$ type of thin film is deposited using a sputtering process or an evaporation process. Then, after forming the movable mirror 55, the thin film in the other area than the movable surface 522A is removed by lift-off.

Figure 8E:
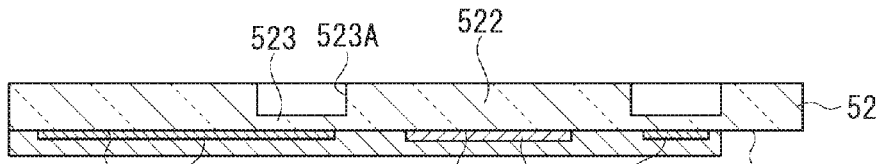
Figure 8F:
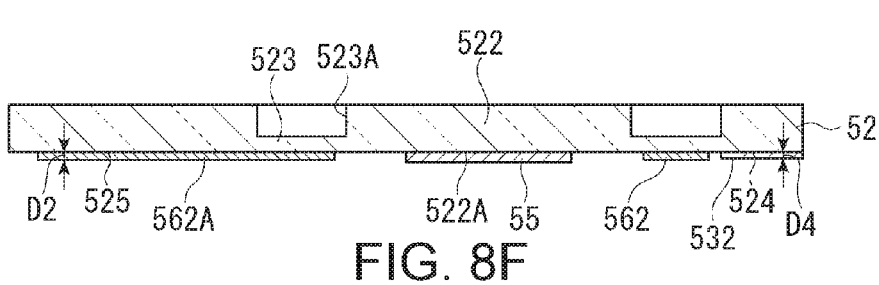

Subsequently, as shown in FIG. 8E, a resist 62 (a lift-off pattern) is formed on the movable substrate 52 in an area other than the formation section of the second bonding film 532 using a photolithography process or the like, and then a plasma-polymerized film using polyorganosiloxane with a thickness dimension D4 is deposited using a plasma CVD process or the like. Then, by removing the resist 62, the second bonding film 532 is formed on the second bonding surface 524 as shown in FIG. 8F.

According to the process described above, the movable substrate 52 is formed.

5-3. Bonding Process

Subsequently, the substrates 51, 52 respectively formed in the fixed substrate manufacturing process and the movable substrate manufacturing process are bonded to each other. Specifically, in order to provide activation energy to the plasma-polymerized films constituting the bonding films 53 formed respectively on the bonding surfaces 515, 524 of the respective substrates 51, 52, an $O_2$ plasma process or a UV process is performed. The $O_2$ plasma process is performed for 30 seconds in the condition in which the $O_2$ flow rate is 30 cc/minute, the pressure is 27 Pa, and the RF power is 200 W. Further, the UV process is performed for 3 minutes using excimer UV (wavelength of 172 nm) as the UV light source. After providing the activation energy to the plasma-polymerized films, alignment of the two substrates 51, 52 is performed, then load is applied to the substrates 51, 52 overlapped with each other on the respective bonding surfaces 515, 524 via the respective bonding films 531, 532 to thereby bond the substrates 51, 52 to each other.

Here, the first conductive electrode 563, the second extraction electrode 562A, the first bonding film 531, and the second bonding film 532 are formed so that the sum of the thickness dimension D1 of the first conductive electrode 563 and the thickness dimension D2 of the second extraction electrode 562A is greater than the sum of the thickness dimension D3 of the first bonding film 531 and the thickness dimension D4 of the second bonding film 532 before bonding the substrates 51, 52 to each other.

Further, in the bonded state of the substrates 51, 52 in which the first bonding film 531 and the second bonding film 532 are bonded to each other, the first electrode surface 516 and the second electrode surface 525 have pressure contact with each other, and therefore, the sum of the thickness dimension D1 of the first conductive electrode 563 and the thickness dimension D2 of the second extraction electrode 562A between the first electrode surface 516 and the second electrode surface 525 is reduced from the value before the bonding to be equal to the sum of the thickness dimension D3 of the first bonding film 531 and the thickness dimension D4 of the second bonding film 532.

According to the process described above, the etalon 5 is manufactured.

6. Functions and Advantages of First Embodiment

According to the first embodiment described above, the following advantages can be obtained.

According to the present embodiment, since the first conductive electrode 563 formed on the first electrode surface 516 and the second extraction electrode 562A of the second electrode 562 formed on the second electrode surface 525 have contact with each other in the bonded state of the substrates 51, 52, it is not required to form an existing Ag paste described above or the like for electrically connecting the electrodes to each other, and therefore, it is possible to electrically connect the electrodes 562, 563 to each other with a simple configuration. In other words, the electrical connection between the electrodes 561, 562 can be made possible only by bonding the substrates 51, 52 to each other via the bonding films 531, 532 without requiring to separately provide the configuration for electrically connecting the electrodes 562, 563 to each other.

Further, the first electrode surface 516 and the first bonding surface 515 are coplanar with each other, and the second electrode surface 525 and the second bonding surface 524 are coplanar with each other. Therefore, in the manufacturing process, the first bonding surface 515 and the first electrode surface 516, or the second bonding surface 524 and the second electrode surface 525 can simultaneously be manufactured, and thus the manufacturing process can be simplified.

Further, before bonding the fixed substrate 51 and the movable substrate 52 to each other, the sum of the thickness dimension D1 of the first conductive electrode 563 and the thickness dimension D2 of the second extraction electrode 562A is larger than the sum of the thickness dimensions (D3+D4) of the bonding films 531, 532, and the first conductive electrode 563 and the second extraction electrode 562A have pressure contact with each other to thereby have surface contact with each other in the bonding process. Therefore, the first conductive electrode 563 and the second extraction electrode 562A can electrically be connected to each other in a reliable manner, and thus the connection reliability can be enhanced.

Further, in the plan view, the first bonding surface 515 and the second bonding surface 524 bonded to each other with the bonding films 531, 532 are disposed between the areas provided with the first electrode surface 516 and the second electrode surface 525 and the displacement section 521. Therefore, as described above, even in the case in which the first conductive electrode 563 and the second extraction electrode 562A have pressure contact with each other, the stress due to the pressure contact is not transmitted to the displacement section 521, and the deflection of the connection holding section 523 and the tilt of the movable section 522 can be prevented.

Second Embodiment

A second embodiment according to the invention will hereinafter be explained with reference to FIGS. 9 and 10.

Figure 9:
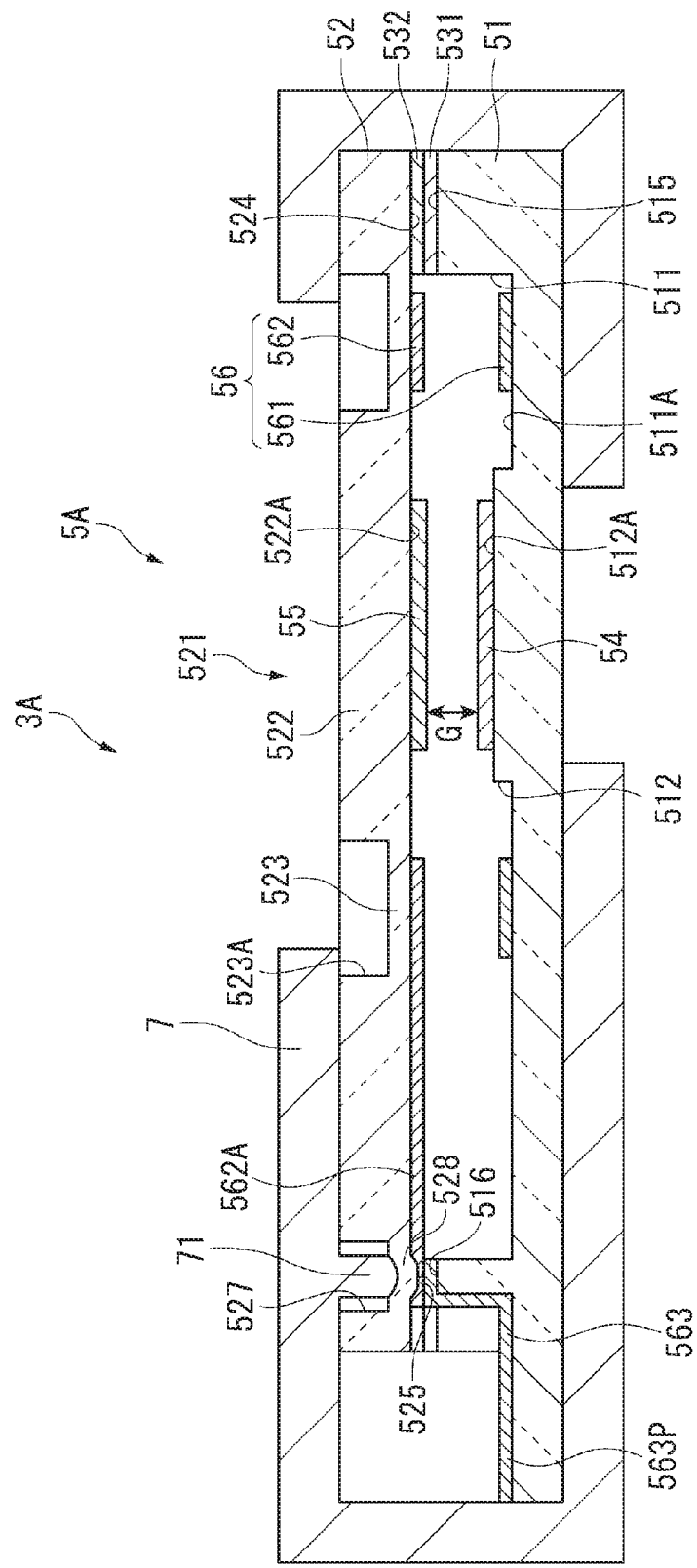
FIG. 9 is a schematic cross-sectional view of an etalon according to a second embodiment of the invention in a condition of being housed in a housing chassis.
Figure 10:
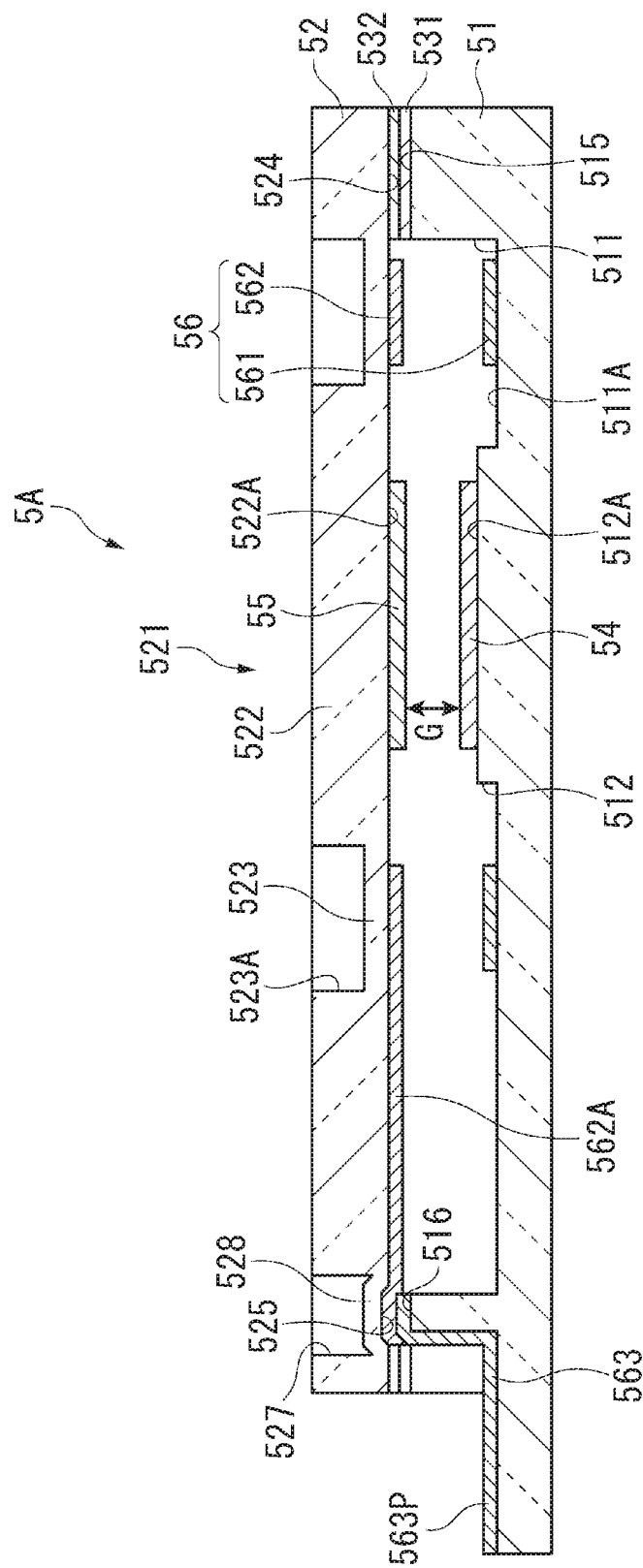
FIG. 10 is a schematic cross-sectional view of the etalon according to the second embodiment.

FIG. 9 is a schematic cross-sectional view of the etalon 5A according to the present embodiment in a condition of being housed in a housing chassis 7, and FIG. 10 is a schematic cross-sectional view showing the etalon 5A before housed in the housing chassis 7.

It should be noted that in the following explanation the constituents identical to those of the first embodiment will be denoted by the same reference symbols, and the explanation therefor will be omitted.

The colorimetric sensor 3A according to the present embodiment is provided with the housing chassis 7 besides the light receiving element 31 (see FIG. 1), the voltage control section 6 (see FIG. 1), and the etalon 5A.

The movable substrate 52 of the etalon 5A is provided with a groove section 527 formed at a position corresponding to the second electrode surface 525. Therefore, since a thin-wall section 528 (a flexible section) is formed between the second electrode surface 525 and the bottom surface of the groove section 527, the thin-wall section 528 is provided with flexibility. Thus, since the first conductive electrode 563 and the second extraction electrode 562A are stacked in the bonding process, the thin-wall section 528 is deformed in the direction away from the fixed substrate 51.

Here, the first conductive electrode 563 and the second extraction electrode 562A have pressure contact with each other due to the elastic force of the thin-wall section 528.

Further, as shown in FIG. 9, the housing chassis 7 is provided with a pressing section 71 for pressing the bottom surface of the groove section 527. Further, if the etalon 5A is housed in the housing chassis 7, since the pressing section 71 presses the bottom surface of the groove section 527, the electrodes 562A, 563 between the first electrode surface 516 and the second electrode surface 525 are further pressed to have pressure contact with each other, and the electrical connection is assured in a more reliable manner.

According to the second embodiment described above, the following advantages can be obtained besides the advantages substantially the same as those of the first embodiment.

According to the present embodiment, since the thin-wall section 528 is deformed in the direction away from the first electrode surface 516 when the substrates 51, 52 are bonded to each other via the bonding films 531, 532, the second electrode surface 525 is biased toward the first electrode surface 516 due to the elastic force of the thin-wall section 528. Therefore, the first conductive electrode 563 and the second extraction electrode 562A formed respectively on the electrode surfaces 516, 525 have pressure contact with each other, and can electrically be connected to each other in a more reliable manner.

Further, the etalon 5A is housed in the housing chassis 7, and the pressing section 71 of the housing chassis 7 presses the thin-wall section 528 toward the first electrode surface 516. Therefore, the first conductive electrode 563 and the second extraction electrode 562A formed respectively on the electrode surfaces 516, 525 have pressure contact with each other, and can have more reliable surface contact with each other, and can electrically be connected to each other in a reliable manner. Further, in the etalon 5A, even in the case in which an individual difference occurs in the shape thereof, the first conductive electrode 563 of the first electrode 561 and the second extraction electrode 562A of the second electrode 562 formed on the respective electrode surfaces 516, 525 can electrically be connected to each other in a reliable manner.

Modifications of Embodiments

It should be noted that the invention is not limited to the embodiments described above, but includes modifications and improvements within a range where the advantages of the invention can be achieved.

For example, although in the embodiments described above there is adopted the configuration in which the electrostatic actuator 56 displaces the displacement section 521, other drive mechanisms can also be used. For example, as shown in FIG. 11, it is also possible to move the displacement section 521 using a piezoelectric actuator 57.

Figure 11:
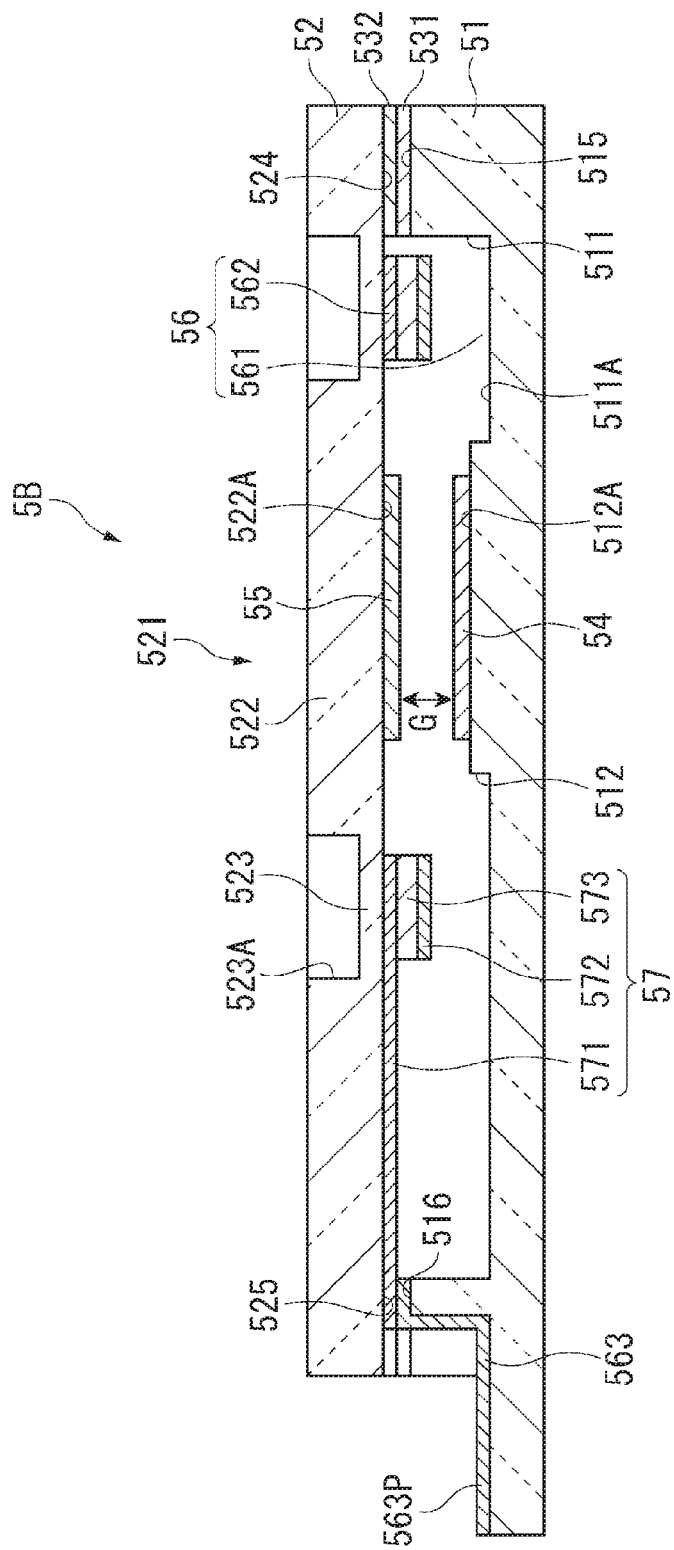
FIG. 11 is a schematic cross-sectional view of an etalon according to a modified example of the embodiment of the invention.

In the etalon 5B shown in FIG. 11, the piezoelectric actuator 57 is disposed on the surface of the connection holding section 523 of the movable substrate 52 opposed to the fixed substrate 51. The piezoelectric actuator 57 is provided with a pair of electrodes 571, 572, and a piezoelectric body 573 sandwiched by the electrodes 571, 572.

Further, among the pair of electrodes, one electrode 571 is wired along an area opposed to the second extraction formation section, extends to the second electrode surface 525, and is then connected to the first conductive electrode 563 disposed on the first electrode surface 516 in a surface contact manner.

Although not shown in the drawings, it is possible for the other electrode 572 to be connected to another first conductive electrode separately disposed on the fixed substrate 51 using the same configuration.

According to such a configuration, when applying a voltage to the pair of electrodes 571, 572, the piezoelectric body 573 converts the voltage applied thereto into a force to thereby expand or contract, and therefore, the displacement section 521 can be moved.

Although in each of the embodiments described above, the explanation is presented assuming that the first substrate according to the invention is the fixed substrate 51, and the second substrate according to the invention is the movable substrate 52, it is also possible to assume that the first substrate is the movable substrate 52, and the second substrate is the fixed substrate 51.

Although in each of the embodiments the first bonding surface 515 and the second bonding surface 524 are bonded to each other via the first bonding film 531 and the second bonding film 532, the bonding surfaces can be bonded only with the first bonding film 531.

Although in each of the embodiments the height dimension from the first reference surface F1 to the first electrode surface 516 and the height dimension from the first reference surface F1 to the first bonding surface 515 are the same dimension, and the height dimension from the second reference surface F2 to the second electrode surface 525 and the height dimension from the second reference surface F2 to the second bonding surface 524 are the same dimension, the invention is not limited thereto. For example, the first electrode surface 516 and the first bonding surface 515 can be formed at different planar heights, and the second electrode surface 525 and the second bonding surface 524 can be formed at different planar heights. Also in this case, by controlling the thickness dimension of the first conductive electrode 563 or the second extraction electrode 562A, the same advantage as in the embodiments described above can be obtained.

Although in the second embodiment described above the colorimetric sensor 3A provided with the housing chassis 7 is described as an example, a configuration without the housing chassis 7 can also be adopted. In this configuration, the first electrode surface 516 pushes up the thin-wall section 528 of the movable substrate 52 in the bonded state of the substrates 51, 52 to thereby make the elastic force act on the thin-wall section 528, and thus the electrodes 562A, 563 can have pressure contact with each other due to the elastic force to thereby electrically be connected to each other.

Further, although the example of providing the pressing section 71 to the housing chassis 7 is described, the configuration of, for example, separately disposing the pressing section for pressing the thin-wall section 528 in the colorimetric sensor 3 can also be adopted.

Further, although in the second embodiment described above there is cited the configuration in which the thin-wall section 528 having a diaphragm shape is formed only in the portion corresponding to the second electrode surface 525 to thereby form the flexible section according to the invention, the invention is not limited thereto. It is also possible to adopt a configuration of, for example, bonding the peripheral edge of the second electrode surface 525 to the movable substrate 52 having a thin plate shape with the bonding films 531, 532 to thereby provide flexibility only to the inside area of the second electrode surface 525.

Further, although in each of the embodiments described above there is shown an example in which the mirror fixation surface 512A of the mirror fixation section 512 opposed to the movable substrate 52 is formed nearer to the movable substrate 52 than the electrode fixation surface 511A, the invention is not limited thereto. The height positions of the electrode fixation surface 511A and the mirror fixation surface 512A are arbitrarily set in accordance with the dimension of the gap between the fixed mirror 54 fixed to the mirror fixation surface 512A and the movable mirror 55 formed on the movable substrate 52, the dimension of a distance between the first drive electrode 561 and the second drive electrode 562, the thickness dimensions of the fixed mirror 54 and the movable mirror 55, and so on. Therefore, there can be adopted, for example, a configuration in which the electrode fixation surface 511A and the mirror fixation surface 512A are formed coplanar with each other, or a configuration in which the mirror fixation groove shaped like a cylindrical recessed groove is formed in the central portion of the electrode fixation surface 511A, and the mirror fixation surface is formed on the bottom surface of the mirror fixation groove.

Further, in the case in which the gap (an inter-electrode gap) between the electrodes 561, 562 is larger than the gap (inter-mirror gap) between the mirrors 54, 55, a high drive voltage becomes necessary for varying the inter-mirror gap. In contrast thereto, in the case in which the inter-mirror gap is larger than the inter-electrode gap as described above, the drive voltage for varying the inter-mirror gap can be reduced to thereby achieve electric power reduction. Further, the variable wavelength interference filter having such a configuration has a large inter-mirror gap, and is therefore effective particular to the spectral characteristics measurement in a long wavelength range, and can be incorporated in a module for performing infrared light analysis used in gas analysis and so on or optical communication.

Although the colorimetric device 1 is cited as an example of the optical analysis device according to the invention, the variable wavelength interference filter, the optical module, and the optical analysis device according to the invention can be used in a variety of fields besides the above.

For example, they can be used as an optical base system for detecting presence of a specific substance. As such a system, there can be cited, for example, an in-car gas leak detector adopting a spectroscopic measurement method using the variable wavelength interference filter according to the invention and detecting a specific gas with high sensitivity, and a gas detection device such as an optoacoustic noble-gas detector for breath-testing.

An example of such a gas detection device will hereinafter be explained with reference to the accompanying drawings.

Figure 12:
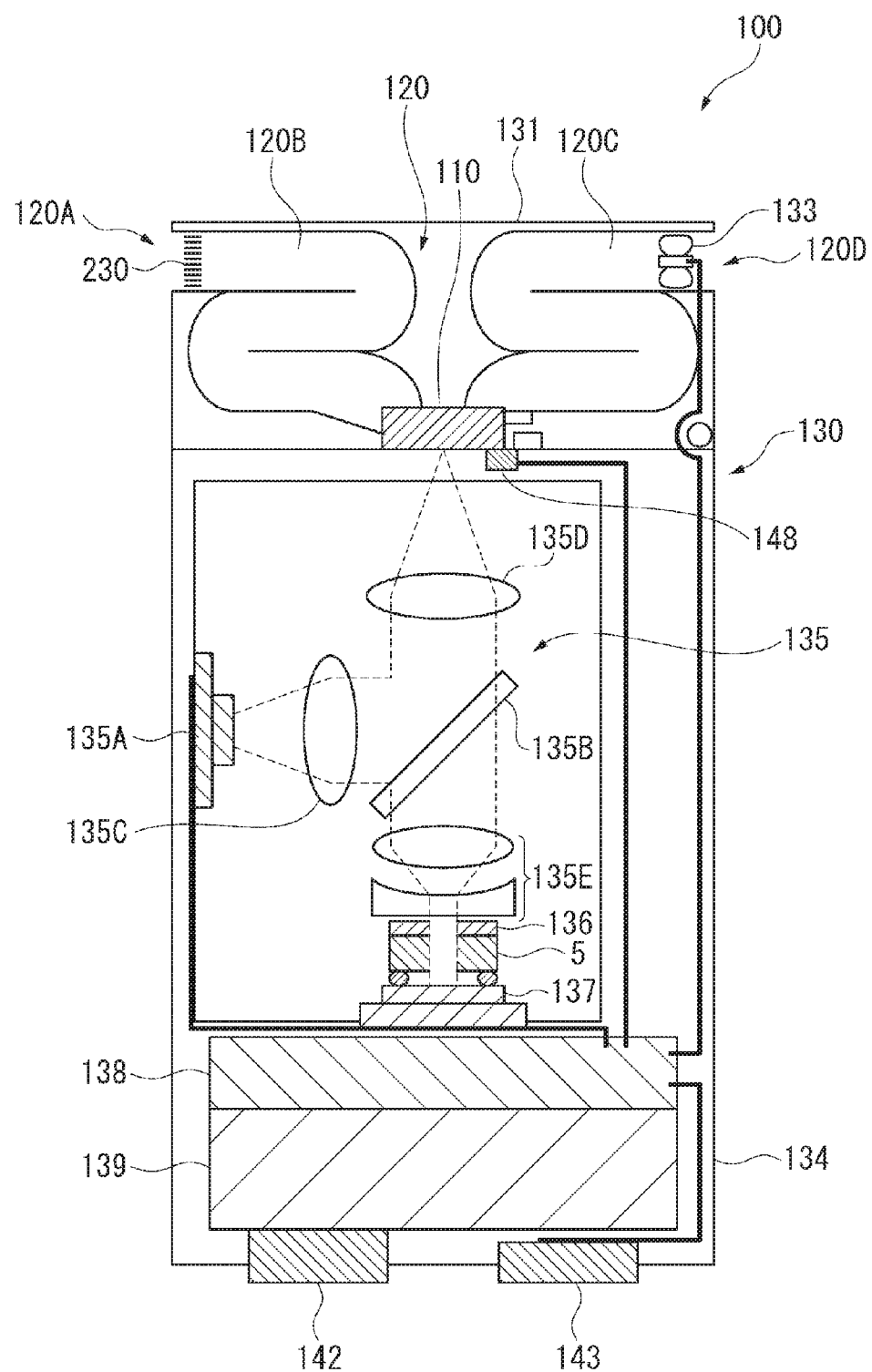
FIG. 12 is a schematic diagram of a gas detection device as another example of an optical analysis device according to an embodiment of the invention.

FIG. 12 is a schematic diagram showing an example of a gas detection device provided with the variable wavelength interference filter.

Figure 13:
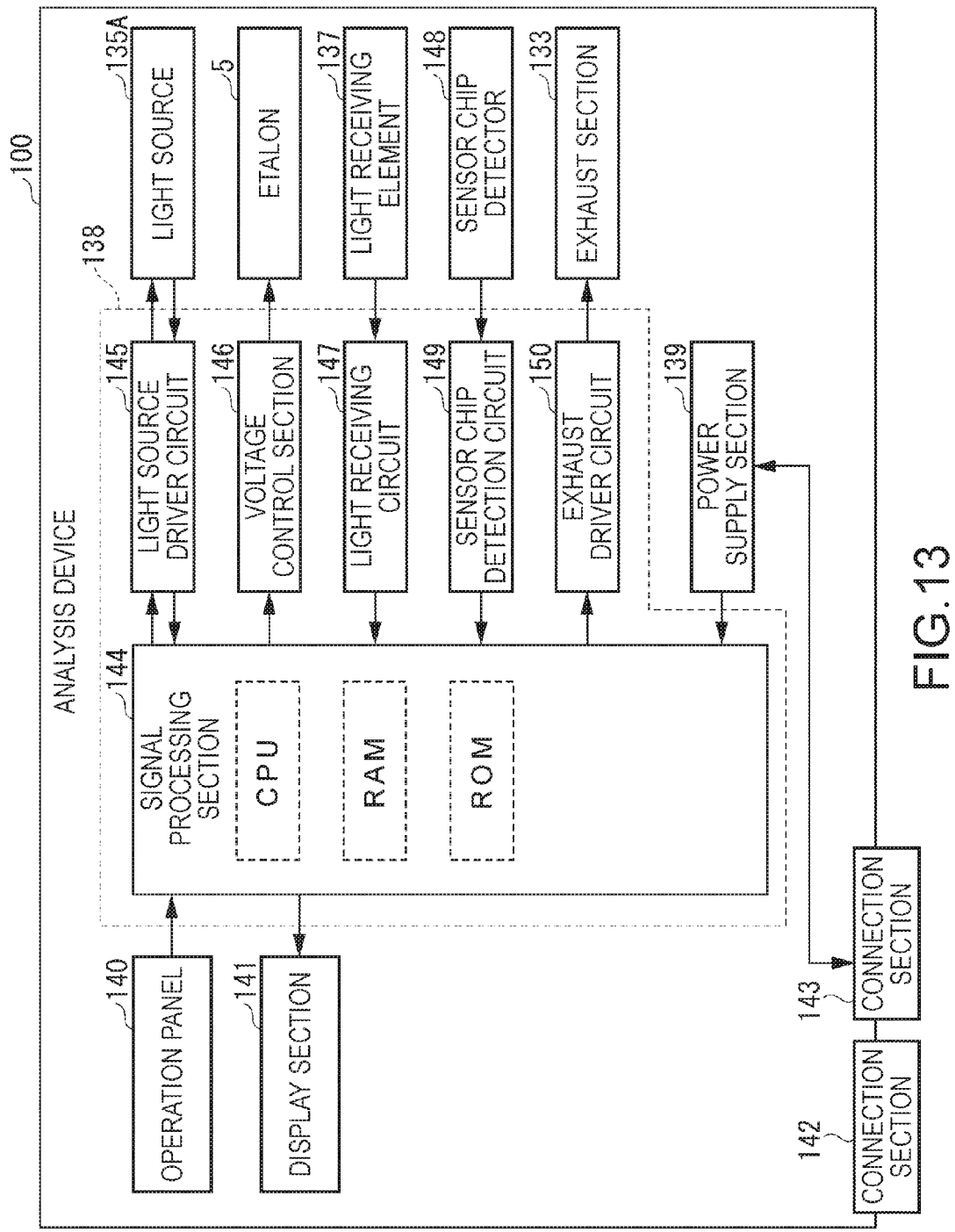
FIG. 13 is a block diagram of the gas analysis device shown in FIG. 12.

FIG. 13 is a block diagram showing a configuration of the control system of the gas detection device shown in FIG. 12.

As shown in FIG. 12, the gas detection device 100 is configured including a sensor chip 110, a channel 120 provided with a suction port 120A, a suction channel 120B, an exhaust channel 120C, and an exhaust port 120D, and a main body 130.

The main body 130 is composed of a detection section (an optical module) including a sensor section cover 131 having an opening to which the channel 120 is detachably attached, an exhaust section 133, a housing 134, an optical section 135, a filter 136, the etalon 5 (the variable wavelength interference filter), a light receiving element 137 (a light receiving section), and so on, a control section 138 for processing the signal thus detected and controlling the detection section, a power supply section 139 for supplying electrical power, and so on. Further, the optical section 135 is composed of a light source 135A for emitting light, a beam splitter 135B for reflecting the light, which is input from the light source 135A, toward the sensor chip 110, and transmitting the light, which is input from the sensor chip, toward the light receiving element 137, and lenses 135C, 135D, and 135E. It should be noted that although the configuration using the etalon 5 is cited as an example, configurations using the etalons 5A, 5B described above can also be adopted.

Further, as shown in FIG. 13, on the surface of the gas detection device 100, there are disposed an operation panel 140, a display section 141, a connection section 142 for an interface with the outside, and a power supply section 139. In the case in which the power supply section 139 is a secondary cell, a connection section 143 for the battery charge can also be provided.

Further, as shown in FIG. 13, the control section 138 of the gas detection device 100 is provided with a signal processing section 144 composed of a CPU and so on, a light source driver circuit 145 for controlling the light source 135A, a voltage control section 146 for controlling the etalon 5, a light receiving circuit 147 for receiving the signal from the light receiving element 137, a sensor chip detection circuit 149 for receiving the signal from a sensor chip detector 148 for reading a code of a sensor chip 110 and detecting presence or absence of the sensor chip 110, an exhaust driver circuit 150 for controlling the exhaust section 133, and so on.

Then, an operation of the gas detection device 100 described above will hereinafter be explained.

The sensor chip detector 148 is disposed in the sensor section cover 131 in the upper part of the main body section 130, and the sensor chip detector 148 detects presence or absence of the sensor chip 110. When detecting the detection signal from the sensor chip detector 148, the signal processing section 144 determines that it is a condition in which the sensor chip 110 is attached, and outputs a display signal for displaying that the detection operation can be performed to the display section 141.

Then, if, for example, the user operates the operation panel 140, and the operation panel 140 outputs an instruction signal indicating that the detection process will be started to the signal processing section 144, the signal processing section 144 firstly outputs the signal for operating the light source to the light source driver circuit 145 to operate the light source 135A. When the light source 135A is driven, the light source 135A emits a laser beam with a single wavelength and stable linearly polarized light. Further, the light source 135A incorporates a temperature sensor and a light intensity sensor, and the information thereof is output to the signal processing section 144. Then, if the signal processing section 144 determines that the light source 135A is in a stable operation based on the temperature and the light intensity input from the light source 135A, the signal processing section 144 controls the exhaust driver circuit 150 to operate the exhaust section 133. Thus, the gaseous sample including the target material (the gas molecule) to be detected is guided from the suction port 120A to the suction channel 120B, inside the sensor chip 110, the exhaust channel 120C, and the exhaust port 120D.

Further, the sensor chip 110 is a sensor incorporating a plurality of sets of metal nano-structures, and using localized surface plasmon resonance. In such a sensor chip 110, an enhanced electric field is formed between the metal nano-structures due to the laser beam, and when the gas molecules enter the enhanced electric field, the Raman scattered light including the information of the molecular vibration and the Rayleigh scattered light are generated.

The Rayleigh scattered light and the Raman scattered light pass through the optical section 135 and then enter the filter 136, and the Rayleigh scattered light is separated by the filter 136, and the Raman scattered light enters the etalon 5. Then, the signal processing section 144 controls the voltage control section 146 to control the voltage applied to the etalon 5 to thereby make the etalon 5 disperse the Raman scattered light corresponding to the gas molecules to be the detection object. After then, if the light thus dispersed is received by the light receiving element 137, the light reception signal corresponding to the received light intensity is output to the signal processing section 144 via the light receiving circuit 147.

The signal processing section 144 compares the spectrum data of the Raman scattered light corresponding to the gas molecule to be the detection object obtained as described above with the data stored in the ROM to thereby determine whether or not it is the target gas molecule, and thus the substance is identified. Further, the signal processing section 144 makes the display section 141 display the result information, or outputs it from the connection section 142 to the outside.

It should be noted that although in FIGS. 12 and 13 the gas detection device 100 for dispersing the Raman scattered light with the etalon 5, and performing the gas detection based on the Raman scattered light thus dispersed is cited as an example, it is also possible to use it as a gas detection device for identifying the gas type by detecting the absorbance unique to the gas. In this case, the gas is made to flow into the sensor, and the gas sensor for detecting the light absorbed by the gas in the incident light is used as the optical module according to the invention. Further, the gas detection device for analyzing and determining the gas flowing into the sensor with such a gas sensor is cited as the optical analysis device according to the invention. It is possible to detect the component of the gas using the variable wavelength interference filter according to the invention also in such a configuration.

Further, as the system for detecting the presence of the specific substance, besides the gas detection described above, there can be cited a substance component analysis device such as a non-invasive measurement device of sugar group using near-infrared dispersion or a non-invasive measurement device of the information of food, biological object, or mineral.

Hereinafter, as an example of the substance component analysis device described above, a food analysis device will be explained.

Figure 14:
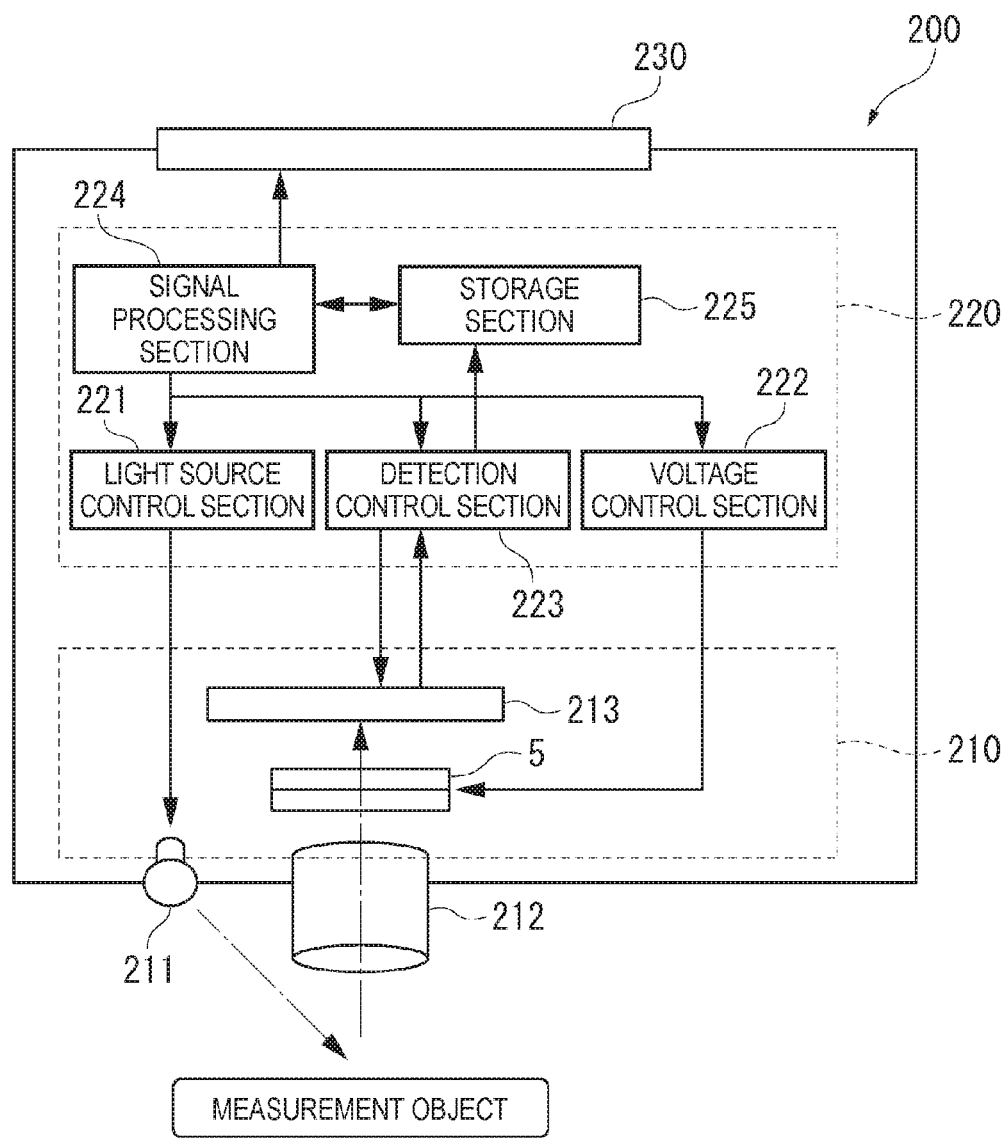
FIG. 14 is a block diagram showing a configuration of a food analysis device as another example of the optical analysis device according to an embodiment of the invention.

FIG. 14 is a diagram showing a schematic configuration of the food analysis device as an example of the optical analysis device using the etalon 5. It should be noted that although the etalon 5 is used here, the configuration using the etalon 5A, 5B can also be adopted.

As shown in FIG. 14, the food analysis device 200 is provided with a detector 210 (the optical module), a control section 220, and a display section 230. The detector 210 is provided with a light source 211 for emitting light, an image pickup lens 212 to which the light from a measurement object is introduced, the etalon 5 (the variable wavelength interference filter) for dispersing the light thus introduced from the image pickup lens 212, and an image pickup section 213 (light receiving section) for detecting the light thus dispersed.

Further, the control section 220 is provided with a light source control section 221 for performing lighting/extinction control of the light source 211 and brightness control when lighting, a voltage control section 222 for controlling the etalon 5, a detection control section 223 for controlling the image pickup section 213 and obtaining a spectral image picked up by the image pickup section 213, a signal processing section 224, and a storage section 225.

In the food analysis device 200, when the system is started up, the light source control section 221 controls the light source 211, and the light source 211 irradiates the measurement object with light. Then, the light reflected by the measurement object passes through the image pickup lens 212 and then enters the etalon 5. The voltage with which the etalon 5 can disperse the light into desired wavelengths is applied to the etalon 5 under the control of the voltage control section 222, and the light thus dispersed is picked up by the image pickup section 213 constituted by, for example, a CCD camera. Further, the light thus picked up is stored in the storage section 225 as the spectral image. Further, the signal processing section 224 controls the voltage control section 222 to vary the voltage value to be applied to the etalon 5 to thereby obtain the spectral image corresponding to each wavelength.

Then, the signal processing section 224 performs an arithmetic process on the data of each pixel in each of the images stored in the storage section 225 to thereby obtain the spectrum in each pixel. Further, the storage section 225 stores, for example, information related to component of food corresponding to the spectrum, and the signal processing section 224 analyzes the data of the spectrum thus obtained based on the information related to the food stored in the storage section 225, and then obtains the food component included in the detection object and the content thereof. Further, the calorie of the food and the freshness thereof can also be calculated based on the food component and the content thus obtained. Further, by analyzing the spectral distribution in the image, it is possible to perform extraction of the portion with low freshness in the food as a test object, and further, it is also possible to perform detection of a foreign matter included in the food.

Then, the signal processing section 224 performs a process of making the display section 230 display the information of the components, the contents, the calorie, the freshness, and so on of the food as the test object obtained as described above.

Further, in FIG. 14, an example of the food analysis device 200 is shown. It is also possible to use substantially the same configuration as the non-invasive measurement device of the other information as described above. For example, it can be used as a biological analysis device for analyzing a biological component such as measurement and analysis of a biological fluid such as blood. If as such a biological analysis device, for example, a device of detecting ethyl alcohol is provided as a device of measuring the biological fluid component such as blood, the device can be used as a device for detecting the influence of alcohol to the driver to thereby prevent driving under the influence of alcohol. Further, it can also be used as an electronic endoscopic system equipped with such a biological analysis device.

Further, it can also be used as a mineral analysis device for performing component analysis of minerals.

Further, the variable wavelength interference filter, the optical module, and the optical analysis device according to the invention can be applied to the following devices.

For example, it is also possible to transmit data with the light having each of the wavelengths by temporally varying the intensity of the light having each of the wavelengths, and in this case, it is possible to extract the data transmitted with the light having a specific wavelength by dispersing the light having the specific wavelength using the variable wavelength interference filter provided to the optical module, and then making the light receiving section receive the light. Therefore, by processing the data of the light having each of the wavelengths using the optical analysis device equipped with such a data extracting optical module, it is also possible to perform optical communication.

Further, the optical analysis device can be applied to a spectroscopic camera for picking up the spectral image and a spectroscopic analysis device by dispersing the light with the variable wavelength interference filter according to the invention. As an example of such a spectroscopic camera, an infrared camera incorporating the variable wavelength interference filter can be cited.

Figure 15:
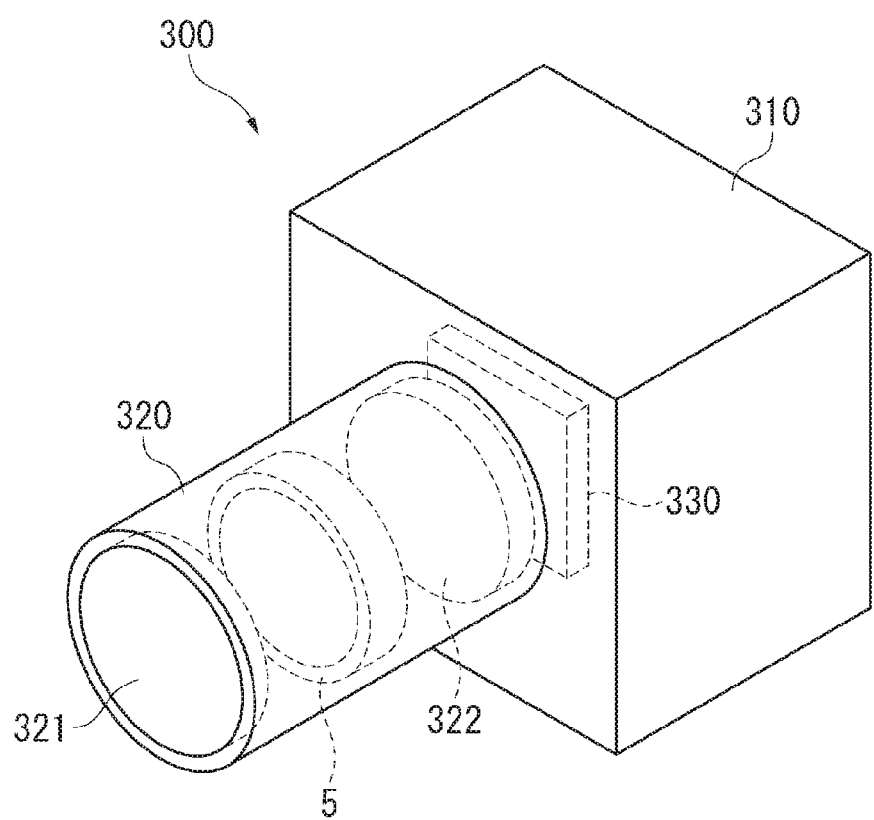
FIG. 15 is a schematic diagram of a spectroscopic camera as another example of the optical analysis device according to an embodiment of the invention.

FIG. 15 is a schematic diagram showing a schematic configuration of the spectroscopic camera. As shown in FIG. 15, the spectroscopic camera 300 is provided with a camera main body 310, an image pickup lens unit 320, and an image pickup section 320.

The camera main boy 310 is a part which is gripped and operated by the user.

The image pickup lens unit 320 is disposed to the camera main body 310, and guides the image light input thereto to the image pickup section 320. Further, as shown in FIG. 15, the image pickup lens unit 320 is configured including an objective lens 321, an imaging lens 322, and the etalon 5 disposed between these lenses.

The image pickup section 320 is formed of a light receiving element, and picks up the image light guided by the image pickup lens unit 320.

In such a spectroscopic camera 300, by transmitting the light with the wavelength to be the imaging object using the etalon 5, the spectral image of the light with a desired wavelength can be picked up.

Further, the variable wavelength interference filter can be used as a band-pass filter, and can also be used as, for example, an optical laser device for dispersing and transmitting only the light with a narrow band centered on a predetermined wavelength out of the light in a predetermined wavelength band emitted by the light emitting element using the variable wavelength interference filter.

Further, the variable wavelength interference filter can be used as a biometric authentication device, and can be applied to, for example, an authentication device of blood vessels, a fingerprint, a retina, an iris, and so on using the light in a near infrared range or a visible range.

Further, the optical module and the optical analysis device can be used as a concentration detection device. In this case, the infrared energy (the infrared light) emitted from the substance is dispersed by the variable wavelength interference filter and is then analyzed, and the concentration of the test object in a sample is measured.

As described above, the variable wavelength interference filter, the optical module, and the optical analysis device according to the invention can be applied to any device for dispersing predetermined light from incident light. Further, since the variable wavelength interference filter according to the invention can disperse the light into a plurality of wavelengths with a single device as described above, the measurement of the spectrum of a plurality of wavelengths and detection of a plurality of components can be performed with accuracy. Therefore, compared to the existing device of taking out desired wavelengths with a plurality of devices, downsizing of the optical module and the optical analysis device can be promoted, and the optical module and the optical analysis device can preferably be used as, for example, the portable or in-car optical device.

Besides the above, specific structures and procedures to be adopted when putting the invention into practice can arbitrarily be replaced with other structures and so on within the range in which the advantages of the invention can be achieved.

What is claimed is:

1. A variable wavelength interference filter comprising:
   a first substrate;
   a second substrate that is disposed so as to oppose the first substrate;
   a first mirror that is disposed between the first substrate and the second substrate;
   a second mirror that is disposed between the first mirror and the second substrate;
   a first electrode that is disposed between the first substrate and the second substrate; and
   a second electrode that is disposed between the first electrode and the second substrate,
   wherein the first substrate has:
      a first electrode surface that is disposed so as to oppose the second substrate;
      a first surface and a second surface that extend from first and second positions of the first electrode surface, respectively, and that are disposed so as to cross the first electrode surface, and the first and second surfaces are opposite to each other; and
      a third surface that extends from the second surface and that is disposed so as to cross the second surface,
   the second substrate has a second electrode surface that is disposed so as to oppose the first substrate,
   the first electrode is disposed between the first electrode surface and second electrode surface so as to cover at least a portion of the second surface and at least a portion of the third surface, and
   the second electrode is connected to the first electrode between the first electrode surface and the second electrode surface.

2. The variable wavelength interference filter according to claim 1,
   wherein the third surface extend in a direction toward an edge of the first substrate.

3. The variable wavelength interference filter according to claim 1,
   wherein the second electrode surface bends in a direction crossing a line connecting between the first surface and the second surface.

4. The variable wavelength interference filter according to claim 1,
   wherein the first substrate has a first bonding surface,
   the second substrate has a second bonding surface so as to oppose the first bonding surface, and
   a bonding film is disposed between the first bonding surface and the second bonding surface.

5. An optical module comprising:
   the variable wavelength interference filter according to claim 1; and
   a light receiver that receives a light from the variable wavelength interference filter.

6. An optical analysis device comprising:
   the variable wavelength interference filter according to claim 1; and
   a processor that is configured to analyze an optical characteristics of a light from the variable wavelength interference filter.

* * * * *